US009678042B2

(12) United States Patent
Kogai et al.

(10) Patent No.: US 9,678,042 B2
(45) Date of Patent: Jun. 13, 2017

(54) SURFACE ACOUSTIC WAVE SENSOR

(71) Applicant: Japan Radio Co., Ltd., Tokyo (JP)

(72) Inventors: Takashi Kogai, Kawagoe (JP); Hiromi Yatsuda, Kawagoe (JP)

(73) Assignee: JAPAN RADIO CO., LTD., Tokyo (JP)

( * ) Notice: Subject to any disclaimer, the term of this patent is extended or adjusted under 35 U.S.C. 154(b) by 420 days.

(21) Appl. No.: 14/355,581

(22) PCT Filed: Nov. 1, 2012

(86) PCT No.: PCT/JP2012/078338
§ 371 (c)(1),
(2) Date: Apr. 30, 2014

(87) PCT Pub. No.: WO2013/065789
PCT Pub. Date: May 10, 2013

(65) Prior Publication Data
US 2014/0305221 A1    Oct. 16, 2014

(30) Foreign Application Priority Data

Nov. 1, 2011  (JP) ................................. 2011-240492
Nov. 1, 2011  (JP) ................................. 2011-240493
Dec. 22, 2011 (JP) ................................. 2011-281611

(51) Int. Cl.
*G01N 29/22*   (2006.01)
*G01N 29/02*   (2006.01)
(Continued)

(52) U.S. Cl.
CPC ......... *G01N 29/222* (2013.01); *G01N 29/022* (2013.01); *G01N 29/024* (2013.01);
(Continued)

(58) Field of Classification Search
CPC .. G01N 29/022–29/036; G01N 29/222; G01N 2291/0255; G01N 2291/0423;
(Continued)

(56) References Cited

U.S. PATENT DOCUMENTS 5,151,110 A *  9/1992  Bein ..................... B01D 53/02
                                                            95/140
5,910,286 A     6/1999  Lipskier
(Continued)

FOREIGN PATENT DOCUMENTS

CN    101052873 A    10/2007
CN    101868916 A    10/2010
(Continued)

OTHER PUBLICATIONS

Office Action issued in Canadian Patent Application No. 2,856,161 dated Nov. 3, 2015, 4 pages.
(Continued)

*Primary Examiner* — Paul West
*Assistant Examiner* — Xin Zhong
(74) *Attorney, Agent, or Firm* — Nixon Peabody, LLP; Khaled Shami

(57) ABSTRACT

A surface acoustic wave sensor of the invention includes: a piezo element that propagates a surface acoustic wave; an electrode that carries out conversion of an electrical signal and a surface acoustic wave; and a porous base member into which liquid infiltrates and which comes into contact with the piezo element.

29 Claims, 19 Drawing Sheets

(51) Int. Cl.
*G01N 29/036* (2006.01)
*G01N 29/024* (2006.01)

(52) U.S. Cl.
CPC ... *G01N 29/036* (2013.01); *G01N 2291/0255* (2013.01); *G01N 2291/0256* (2013.01); *G01N 2291/0423* (2013.01)

(58) Field of Classification Search
CPC ..... G01N 2291/0256; G01N 2291/011; G01N 2291/012; G01N 2291/022–2291/0228
See application file for complete search history.

(56) References Cited

U.S. PATENT DOCUMENTS

| | | | |
|---|---|---|---|
| 2006/0032290 A1 | 2/2006 | Liu | |
| 2008/0289397 A1 | 11/2008 | Hassan et al. | |
| 2010/0236322 A1* | 9/2010 | Kogai | G01N 29/022 73/53.01 |
| 2010/0288014 A1* | 11/2010 | Yao | G01N 29/022 73/24.06 |

FOREIGN PATENT DOCUMENTS

| | | |
|---|---|---|
| JP | 02-122242 | 5/1990 |
| JP | 04-122242 A | 5/1990 |
| JP | 05-281120 A | 10/1993 |
| JP | 2713534 B | 2/1998 |
| JP | 2004-526977 A | 9/2004 |
| JP | 2007-093239 A | 4/2007 |
| JP | 2007-147556 A | 6/2007 |
| JP | 2008-286606 A | 11/2008 |
| JP | 2010025728 A | 2/2010 |
| JP | 2013092446 A | 5/2013 |
| WO | 02/095940 A1 | 11/2002 |
| WO | 2005/064349 A2 | 7/2005 |
| WO | 2008/105918 A2 | 9/2008 |

OTHER PUBLICATIONS

Extended EP search report mailed Jun. 3, 2015 for Application No. 12845886.6. (6 pages).
CN search report mailed Jun. 14, 2015 for Application No. 2012800541410 (12 pages).
Hiromi Yatsuda, Takashi Kogai, Mikihiro Goto, Michael Chard and Dale Athey, "SH-SAW Biosensor for POCT", 40th EM Symposium, May 19, 2011, pp. 29-32.
International Search Report in PCT/JP2012/078338, Japanese Patent Office, mailed Jan. 15, 2013.
Notice of Reasons for Rejection, dated May 31, 2016, issued in Japanese Patent Application No. 2011-240493, 9 pages.
Notice of Reasons for Rejection, dated May 31, 2016, issued in Japanese Patent Application No. 2011-240492, 8 pages.

* cited by examiner

SURFACE ACOUSTIC WAVE SENSOR

CROSS REFERENCE TO RELATED APPLICATIONS

This application is the national stage of International Application No. PCT/JP2012/078338, filed Nov. 1, 2012, entitled, "Surface Acoustic Wave Sensor," which claims the benefit of priority of Japanese Patent Application No. 2011-240492 filed on Nov. 1, 2011, Japanese Patent Application No. 2011-240493 filed on Nov. 1, 2011, and Japanese Patent Application No. 2011-281611 filed on Dec. 22, 2011, the contents of which are incorporated herein by reference in their entirety.

TECHNICAL FIELD

Background Art

A SAW (Surface Acoustic Wave; surface acoustic wave) filter is known as one of band-pass filters used in an electronic circuit.

Such a SAW filter has a reduced size and excellent attenuation characteristics and is used in various electronic devices such as portable telephones.

For example, a SAW filter includes an interdigitated array electrode (Inter Digital Transducer; IDT) used to generate a surface acoustic wave (acoustic surface wave) on a piezoelectric element substrate and to detect a surface acoustic wave.

As a technique of a SAW filter, a surface acoustic wave sensor that is formed on a piezoelectric substrate and between an IDT constituting a transmission electrode and an IDT constituting a reception electrode and is provided with a detection region (region serving as sensor surface) into which liquid serving as an analyte is introduced, is disclosed in Patent Document 1.

In Patent Document 1, a surface acoustic wave sensor is disclosed which includes: a piezoelectric substrate; transmission-and-reception electrode including a transmission electrode that is formed on the surface of the piezoelectric substrate in a predetermined pattern and performs transmission of a surface acoustic wave and a reception electrode that is formed on the surface of the piezoelectric substrate in a predetermined pattern and performs reception of the surface acoustic wave; a detection region which is formed between the transmission electrode and the reception electrode and into which liquid serving as an analyte is introduced; and a sealing structure that covers so as to tightly seal the transmission-and-reception electrode from the exterior.

In the surface acoustic wave sensor, propagation characteristics of a surface acoustic wave from the transmission electrode to the reception electrode vary depending on the liquid serving as an analyte which is introduced into the detection region.

Moreover, the surface acoustic wave sensor is provided with a dummy electrode that is made of a metal, is formed at at least one of intermediates between the transmission electrode and the detection region and between the detection region and the reception electrode, and is used to cause energy of a surface acoustic wave to concentrate into the surface of the piezoelectric substrate.

The surface acoustic wave sensor that is on the piezoelectric substrate and between the IDT constituting the transmission electrode and the IDT constituting the reception electrode and is provided with the detection region into which liquid serving as an analyte is introduced (region serving as sensor surface), is disclosed in Patent Document 1.

In the surface acoustic wave sensor, as a result of measuring variation in propagation velocity (or phase) of the surface acoustic wave which is caused by dropping a liquid sample on an inspection region, it is determined whether or not the liquid sample includes an analyte, and the concentration or the like of the analyte is detected.

PRIOR ART DOCUMENTS

Patent Documents

[Patent Document 1] Japanese Unexamined Patent Application, First Publication No. 2008-286606

SUMMARY OF INVENTION

Problems to be Solved by the Invention

However, the surface acoustic wave sensor disclosed in Patent Document 1 has been used in a method of directly dropping solution on the sensor surface or a method of dipping the sensor surface in solution (dipping).

Therefore, it is necessary to uncover the sensor surface as its structure, and there are problems in that damage such as scratches on the surface thereof easily occurs and it is not possible to carry out simple measurements.

Additionally, it is necessary to reliably cover over the sensor surface with a solution dropping thereon in order to sufficiently ensure accuracy of measurement; however, a method of dropping a solution thereon cannot realize the necessary.

Furthermore, there is a problem in that the solution dropped cannot be maintained because of volatilization or the like in a desired measurement time.

Moreover, since a technique disclosed in Patent Document 1 provides a sealing structure, there is a problem of an increase in the cost of manufacture thereof.

Also, in the technique disclosed in Patent Document 1, in the case where the distance between the transmission electrode and the reception electrode and the width of the detection region are large, when a liquid sample having an analyte with a high concentration is dropped on the detection region, the reaction between the sensor surface and the analyte is saturated.

In the case where the reaction is saturated, since a propagation loss of a surface acoustic wave increases, the amplitude of vibration of the surface acoustic wave becomes small or becomes 0.

In the case where the amplitude of vibration of the surface acoustic wave becomes 0, there is a problem in that it is difficult for the surface acoustic wave sensor to detect an analyte in the liquid sample.

The invention was made with respect to the above-described viewpoint and provides a surface acoustic wave sensor that can carry out simple measurements and improve the accuracy of measurement.

Additionally, the invention provides a surface acoustic wave sensor that can reduce the cost of manufacture thereof.

Moreover, an object of the invention is to provide a surface acoustic wave sensor that easily detects an analyte.

Means for Solving the Problems

The invention was made in order to solve the above problems, and a surface acoustic wave sensor of an aspect of the invention includes: a piezo element that propagates a surface acoustic wave; an electrode (electrode portion) that carries out conversion of an electrical signal and a surface acoustic wave; and a porous base member which is disposed at a propagation path of the surface acoustic wave, is disposed above a detection region of the piezo element into which liquid serving as an analyte is introduced, and into which liquid infiltrates, the liquid having a portion that comes into contact with the detection region which is due to the liquid infiltration by a capillary phenomenon.

It is preferable that the surface acoustic wave sensor of the aspect of the invention further include a sealing structure that prevents the electrode from coming into contact with liquid.

In the surface acoustic wave sensor of the aspect of the invention, it is preferable that the porous base member have a portion that does not overlap the detection region in a plan view.

In the surface acoustic wave sensor of the aspect of the invention, it is preferable that two electrodes be provided, and that the detection region have a short-circuiting reaction region that is electrically connected to one of the two electrodes and an open reaction region that is not electrically connected to the other of the two electrodes.

In the surface acoustic wave sensor of the aspect of the invention, it is preferable that the porous base member allow liquid to infiltrate thereinto due to a capillary phenomenon in a propagation direction of the surface acoustic wave.

In the surface acoustic wave sensor of the aspect of the invention, it is preferable that separate reactants which react with a target be formed and dispersed in directions in which the solution infiltrates into the porous base member.

In the surface acoustic wave sensor of the aspect of the invention, it is preferable that the porous base member include at least one of a reaction layer including a substance that reacts with a target and a filter layer that removes other than a target.

It is preferable that the porous base member have a portion that does not come into contact with the piezo element.

It is preferable that a plurality of electrodes be provided and that reactants that react with each target be provided on the porous base member.

In the surface acoustic wave sensor of the aspect of the invention, it is preferable that a plurality of electrodes be provided and that reactants that react with each target be provided on each porous base member.

In the surface acoustic wave sensor of the aspect of the invention, it is preferable that two electrodes be provided and that the porous base member come into contact with the piezo element with a thin film interposed therebetween, be connected to the porous base member, and have a portion that comes into contact with each electrode is formed of a hydrophobic base member.

In the surface acoustic wave sensor of the aspect of the invention, it is preferable that the piezo element include: a first portion having a region that is not electrically connected to the electrode; and a second portion having a thin film that is electrically connected to the electrode.

In the surface acoustic wave sensor of the aspect of the invention, it is preferable that the porous base member include a first region and a second region, that the first region and the second region be alternately formed in a propagation direction of the surface acoustic wave, and that the infiltration rate in the first region be greater than the infiltration rate in the second region.

In the surface acoustic wave sensor of the aspect of the invention, it is preferable that, in the porous base member, lengths in the propagation direction of the surface acoustic wave in a plurality of the first regions be different from each other.

In the surface acoustic wave sensor of the aspect of the invention, it is preferable that, in the porous base member, lengths in the propagation direction of the surface acoustic wave in a plurality of the second regions be different from each other.

Effects of the Invention

According to the invention, it is possible to provide a surface acoustic wave sensor that can carry out simple measurements and improve the accuracy of measurement.

According to the invention, it is possible to reduce the cost of manufacturing thereof.

According to the invention, since the porous base member that creates a capillary phenomenon is provided at the inspection region, the entirety of the inspection region is not wet at the same time.

For this reason, even in the case where the concentration of analyte in a solution is high, a detection signal is not saturated, and detection of analyte is easy.

EMBODIMENTS FOR CARRYING OUT THE INVENTION

First Embodiment

Hereinafter, an embodiment of the invention will be described in detail with reference to drawings.

Figure 1A:
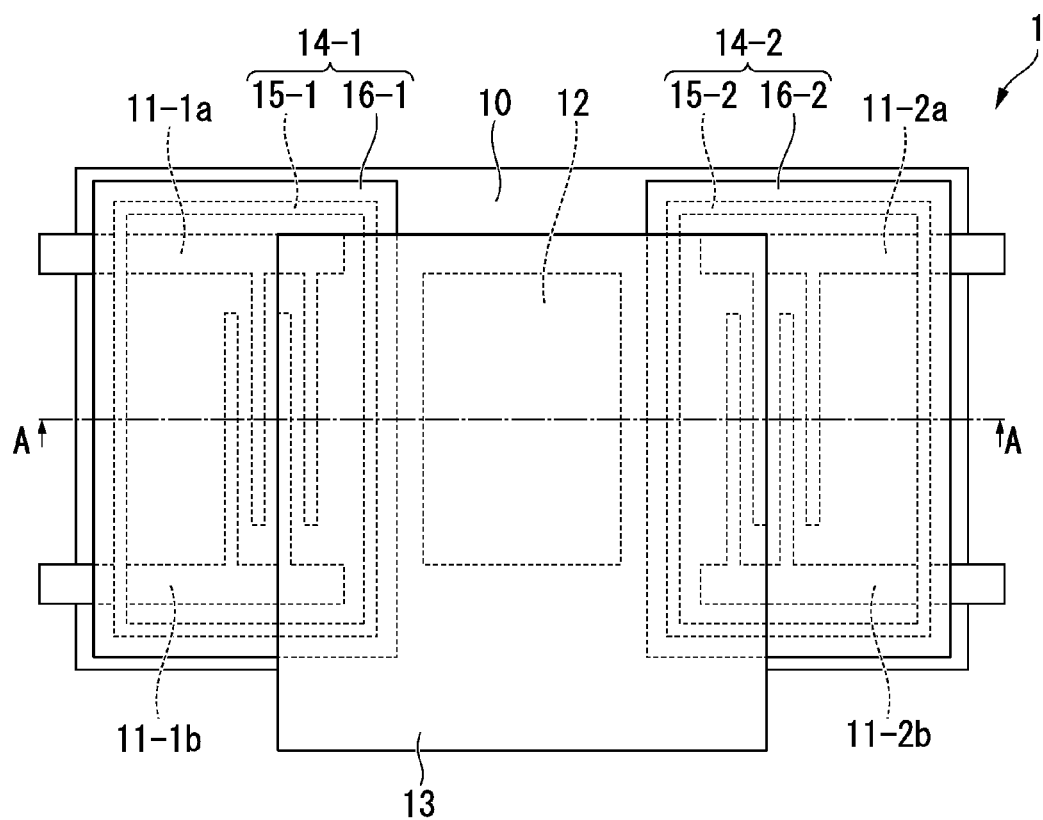
FIG. 1A is a schematic top view showing a SAW sensor according to a first embodiment of the invention.
Figure 1B:
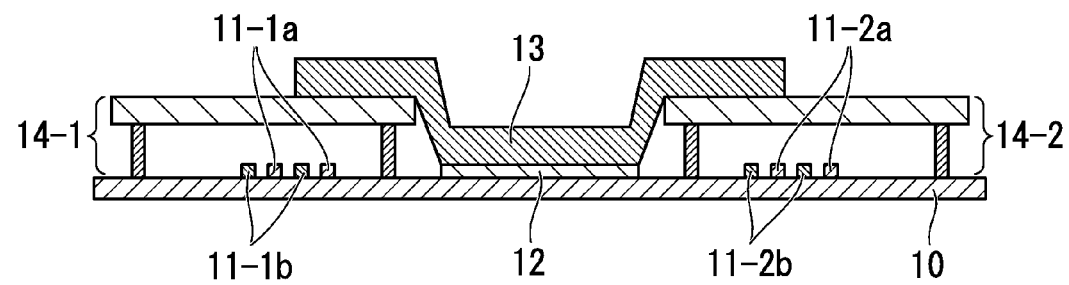
FIG. 1B is a schematic cross-sectional view showing the SAW sensor according to the first embodiment of the invention.

FIGS. 1A and 1B are schematic views showing a SAW sensor according to a first embodiment.

FIG. 1A is a schematic top view showing the SAW sensor 1, and FIG. 1B is a schematic cross-sectional view showing the SAW sensor 1 as seen from the cutting plane A.

The SAW sensor 1 is configured to include a piezoelectric element substrate 10 (piezo element), a transmission electrode 11-1a, a transmission electrode 11-1b, a reception electrode 11-2a, a reception electrode 11-2b, a reaction-region thin film 12, a porous base member 13, a sealing structure 14-1, and a sealing structure 14-2.

The piezoelectric element substrate 10 is a substrate that propagates a SAW.

The piezoelectric element substrate 10 is a quartz substrate.

The transmission electrode 11-1a and the transmission electrode 11-1b are metal electrodes that constitute a transmission electrode and are formed in a comb-shaped pattern.

Hereinbelow, the transmission electrode 11-1a and the transmission electrode 11-1b are referred to as IDT 11-1.

In addition, the reception electrode 11-2a and the reception electrode 11-2b are metal electrodes that constitute reception electrode and is formed of a comb-shaped pattern.

Hereinbelow, the reception electrode 11-2a and the reception electrode 11-2b are collectively referred to as IDT 11-2.

The IDT 11-1 and the IDT 11-2 (collectively referred to as IDT 11) are electrodes that are formed on the piezoelectric element substrate 10.

The IDT 11 is a pair of facing electrodes.

The IDT 11 is configured of, for example, an aluminum thin film.

The reaction-region thin film 12 is a thin film that is produced by vapor deposition of gold.

The reaction-region thin film 12 is a thin film having a surface on which an antibody is supported.

The reaction-region thin film 12 is formed on the piezoelectric element substrate 10 and on the region between the paired IDTs 11 that are provided on the piezoelectric element substrate 10 so as to face each other.

The portion on which the piezoelectric element substrate 10 overlaps the reaction-region thin film 12 is a detection region into which liquid serving as an analyte is introduced (region serves as sensor surface).

The porous base member 13 is a base member that is provided to be in contact with the reaction-region thin film 12.

The porous base member 13 is made of a substance such as cellulose nitrate.

The porous base member 13 is fixed so as to completely cover the reaction-region thin film 12.

For example, the porous base member 13 is fixed to be adhesively attached to the external four corners of the reaction-region thin film 12.

The porous base member 13 holds solution that drops thereon and allows the solution to infiltrate into the inside thereof and the surface thereof.

The porous base member 13 transfers the solution, that dropped thereon, to the inside of the porous base member 13 and the surface of the reaction-region thin film 12 due to a capillary phenomenon, and holds it.

That is, the SAW sensor 1 holds the solution drop inside the porous base member 13 and on the surface of the reaction-region thin film 12.

In the SAW sensor 1, the solution that is transported to the inside of the porous base member 13 makes a specified area of the reaction-region thin film 12 wet.

Here, the specified area is a region having a surface area defined by the portion on which the porous base member 13 overlaps the reaction-region thin film 12.

For example, in the case where the porous base member 13 covers the entire surface of the reaction-region thin film 12, it is the entire region of the reaction-region thin film 12.

An antigen in solution reacts with an antibody that is supported on the reaction-region thin film 12, and an antigen antibody complex is thereby generated on a specified region of the reaction-region thin film 12.

That is, in the reaction-region thin film 12, as a result of dropping a liquid sample including an antigen on the top surface thereof, an antigen-antibody reaction occurs between the antibody that is supported on the reaction-region thin film 12 and the antigen of the liquid sample.

Consequently, an antigen antibody complex in which the antibody that is supported on the reaction-region thin film 12 and the antigen are combined is produced on the reaction-region thin film 12.

In other cases, even other than gold, various materials may be adopted as a material used to form the reaction-region thin film 12 as long as the material can support an antibody.

Additionally, as shown in FIGS. 1A and 1B, since the porous base member 13 is larger than the reaction-region thin film 12, it protrudes from the reaction-region thin film 12; however, the porous base member 13 does not necessarily protrude from the reaction-region thin film 12 as shown in drawings, and it may overlap the reaction-region thin film 12 so as to have the same surface area when seen in a plan view or may be disposed to have a small surface area so as to be located inside of the reaction-region thin film 12 when seen in plan view.

The porous base member 13 is only necessary to be disposed so as to cover the specified region of the reaction-region thin film 12.

The sealing structure 14-1 of the transmission electrode (disposed at the position close to the transmission electrode) includes a sealing wall 15-1 and a seal ceiling 16-1.

Moreover, an adhesive layer that is used to adhesively attach both the sealing wall 15-1 and the seal ceiling 16-1 are provided therebetween, and it is not shown in FIGS. 1A and 1B.

The sealing wall 15-1 is a wall that covers the IDT 11-1 and is formed on the piezoelectric element substrate 10 in a rectangle shape.

The sealing wall 15-1 is formed from, for example, photosensitive resin.

Furthermore, the seal ceiling 16-1 is a ceiling that occludes the upper side of the sealing wall 15-1 and thereby tightly seals the IDT 11-1 from the exterior.

The seal ceiling 16-1 is disposed at the upper side of the sealing wall 15-1 so that the sealing wall 15-1 is located in the flat surface region of the seal ceiling 16-1.

The seal ceiling 16-1 is formed of, for example, a glass substrate.

In particular, an adhesive layer which is not shown in the figure is provided between the sealing wall 15-1 and the seal ceiling 16-1, and adhesively attaches the sealing wall 15-1 to the seal ceiling 16-1 by tight sealing.

The sealing structure 14-1 is a sealing structure that covers and tightly seals the IDT 11-1 from the exterior so as to form a space above the IDT 11-1 and prevents the IDT 11-1 from coming into contact with liquid.

Additionally, similar to the sealing structure 14-1, the sealing structure 14-2 of the reception electrode (provided at the position close to the reception electrode) is a sealing structure that includes a sealing wall 15-2 and a seal ceiling 16-2, covers and tightly seals the IDT 11-2 from the exterior so as to form a space above the IDT 11-2, and prevents the IDT 11-2 from coming into contact with liquid.

Even where there is a variation in an atmosphere (for example, degree of humidity) in the detection region, as a result of adopting the sealing structure 14-1 and the sealing structure 14-2, the IDT 11-1 and the IDT 11-2 are less easily affected by the variation thereof.

Furthermore, a structure in which the porous base member 13 is disposed so as to overlap the sealing structure 14-1 and the seal ceiling of the sealing structure 14-2 is shown in FIGS. 1A and 1B; however, it is not necessary to arrange the porous base member 13 so as to overlap the seal ceiling as long as it is disposed so as to cover the detection region of a sensor on which the reaction-region thin film 12 is placed.

Particularly, in the case of arranging the porous base member 13 so as not to overlap the seal ceiling, even where the porous base member 13 is significantly displaced in a direction in which a surface acoustic wave propagates (displacement), since the sealing structure 14-1 and the sealing structure 14-2 protect the IDT 11-1 and the IDT 11-2, respectively, the IDT is not wet with solution, it does not affect an operation of transmitting an elastic wave or an operation of receiving an elastic wave of the IDT.

Figure 2:
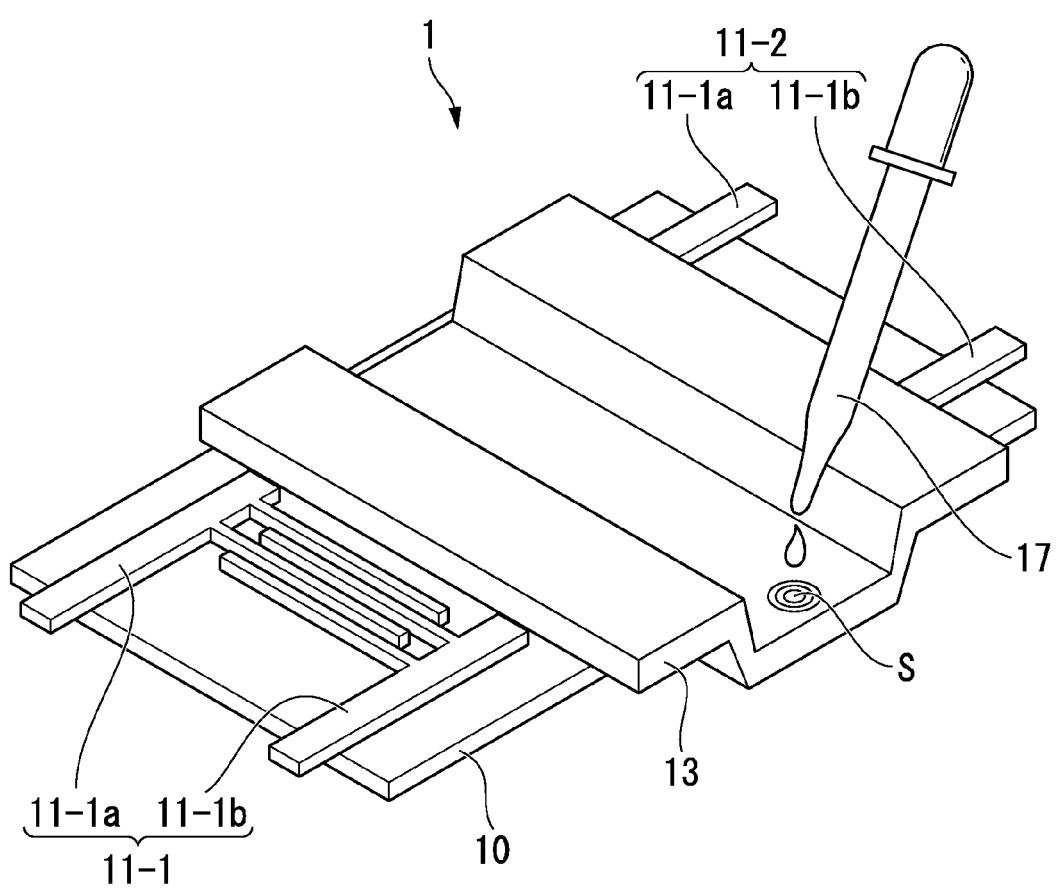
FIG. 2 is a schematic perspective view showing the SAW sensor according to the first embodiment of the invention.

FIG. 2 is a schematic perspective view showing the SAW sensor 1 according to the first embodiment.

In FIG. 2, identical symbols are used for the elements which are identical to those of FIGS. 1A and 1B, and the explanations thereof are omitted here.

In particular, the reaction-region thin film 12, the sealing structure 14-1, and the sealing structure 14-2 which are shown in FIGS. 1A and 1B are omitted in FIG. 2.

A burst signal serving as a transmitting signal is input to the IDT 11-1 from a burst circuit 22 which will be described later.

The IDT 11-1 excites a SAW corresponding to the input burst signal on the surface of the piezoelectric element substrate 10.

The IDT 11-2 converts the SAW that propagated along the surface of the piezoelectric element substrate 10 into an electrical signal.

The IDT 11-2 outputs the received electrical signal (referred to as a detection signal) to a phase-amplitude detecting circuit 23 which will be described later.

Particularly, the region represented by reference letter S indicates part of the porous base member 13 on which solution is to be dropped.

The region S is an area of part of the porous base member 13, which is formed in a direction orthogonal to the direction in which the IDT 11-1 and the IDT 11-2 are arranged and in a direction in which the porous base member 13 extends outward.

When a measurer of the SAW sensor 1 drops solution on the region S by use of, for example, a micropipette 17 shown in FIG. 2, the porous base member 13 transfers the solution that is dropped thereon to the inside of the porous base member 13 and the surface of the reaction-region thin film 12 due to a capillary phenomenon, and holds it.

That is, even where the porous base member 13 has a portion that does not overlap the detection region in a plan view, since the porous base member 13 transfers the solution to the surface of the reaction-region thin film 12 and holding it, it is possible to make the specified region of the reaction-region thin film 12, for example, the entire surface thereof (detection region), wet with the solution that is dropped thereon.

Figure 3:
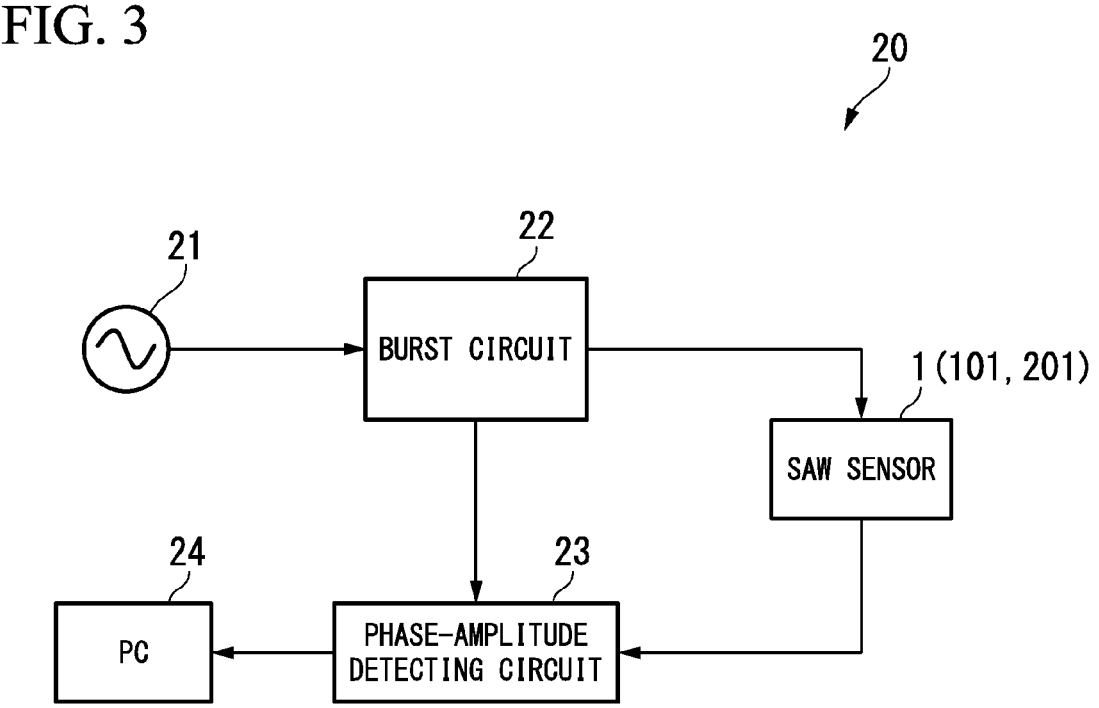
FIG. 3 is a schematic block diagram illustrating a sense circuit of a SAW device according to the first embodiment of the invention.

FIG. 3 is a schematic block diagram illustrating a sense circuit 20 used in solution measurement using the SAW sensor 1.

As shown in FIG. 3, the sense circuit 20 is configured to include the SAW sensor 1, an alternating-current signal source 21, the burst circuit 22, the phase-amplitude detecting circuit 23, and a PC 24 (Personal Computer).

The alternating-current signal source 21 generates a sine wave alternating-current signal of, for example, 250 MHz.

The alternating-current signal source 21 outputs the generated alternating-current signal to the burst circuit 22.

The burst circuit 22 converts the alternating-current signal that is input from the alternating-current signal source 21 into a periodic burst signal.

Here, the period of the burst signal is set to be longer than a time required for propagation of the SAW from the IDT 11-1 to the IDT 11-2 of the surface of the piezoelectric element substrate 10.

The burst circuit 22 outputs the generated burst signal to the IDT 11-1 and the phase-amplitude detecting circuit 23 of the SAW sensor 1.

In other cases, in the case where a disturbing signal such as noise including a direct wave, other bulk wave, or the like with the exception of a main signal included in the signal output from the SAW sensor 1 is sufficiently low, the burst circuit 22 is not necessary, and a continuous wave may be used.

Based on a detection signal input from the IDT 11-2 of the SAW sensor 1 and the burst signal input from the burst circuit 22, the phase-amplitude detecting circuit 23 calculates a phase variation and an amplitude change which are associated with a propagation time that is a time required for propagation of the SAW on the piezoelectric element substrate 10.

Specifically, the phase-amplitude detecting circuit 23 detects a phase variation and attenuation of amplitude which is associated with a required propagation time between the inputting of the burst signal and the inputting of the detection signal.

The phase-amplitude detecting circuit 23 outputs the detected phase variation and the attenuation of amplitude to the PC 24.

Based on the phase variation and the attenuation of amplitude which are input from the phase-amplitude detecting circuit 23, the PC 24 determines the amount of an antigen in a solution that were specifically-reacted with an antibody on the surface and displays the determination result.

Here, the phase variation and the attenuation of amplitude of the SAW will be described.

The SAW is an acoustic wave that concentrates in the vicinity of the surface of the piezoelectric element substrate 10 (the position close to the surface) and propagates.

When a substance adsorbs onto the top surface of the piezoelectric element substrate 10, the mass per unit volume and the degree of viscosity of the top surface thereof vary.

As a result, the propagation velocity and the amplitude of the SAW vary.

For this reason, the propagation time of the SAW varies and the attenuation of amplitude varies.

In the first embodiment, an antigen that is contained in a solution is measured utilizing the variation in phase and variation in attenuation of amplitude.

Specifically, at first, a measurer of the SAW sensor 1 drops a solvent that does not contain an antigen on the region S shown in FIG. 2 and thereby makes the top of the reaction-region thin film 12 wet with the solvent, and measures the phase variation which is associated with the propagation time of the SAW (blank test).

Next, the measurer of the SAW sensor 1 replaces the SAW sensor 1 with another sample (SAW sensor 1), drops the solution of the sample containing an antigen on the region S shown in FIG. 2, and measures the phase variation which is associated with the propagation time thereof.

A difference between the phase variation corresponding to the solvent and the phase variation corresponding to the solution is a variation in phase which is caused by an antigen antibody complex that is generated in the reaction-region thin film 12 due to an antigen-antibody reaction.

The PC 24 has stored the phase variation of the blank test in memory, calculates the difference between the phase variation and the phase variation obtained by dropping of a solution, and thereby calculates the variation in phase.

The PC 24 determines the amount of an antigen contained in solution based on the variation in phase.

Similar to attenuation of amplitude, the PC 24 determines the amount of an antigen contained in solution based on the variation in attenuation of amplitude.

In other cases, if the phase variation of the SAW in the solvent to be used is determined in advance, the measurer does not need to measure the phase variation of the SAW in the solvent.

Furthermore, even in the case where the propagation time of the SAW in the solvent to be used is not determined in advance, the phase and the amplitude which are immediately after dropping of solution containing an antigen are used as a reference, the amount of and the kind of antigen in solution is determined as a result of obtaining the difference between subsequent changes based thereon, and the determination result may be displayed.

As described above, the SAW sensor of first embodiment includes: a piezoelectric element substrate (the piezoelectric element substrate 10) that propagates a surface acoustic wave; electrodes that carry out conversion of an electrical signal and a surface acoustic wave (the IDT 11-1 that carries out conversion of an electrical signal into a surface acoustic wave and the IDT 11-2 that carries out conversion of a surface acoustic wave into an electrical signal); a porous base member (the porous base member 13) which is placed on a transmission path of the surface acoustic wave and comes into contact with a detection region into which liquid serving as an analyte is introduced (the reaction-region thin film 12), and into which liquid infiltrates; and a sealing structure (the sealing structure 14-1 and the sealing structure 14-2) that prevents the electrode from coming into contact with liquid.

Accordingly, since a dropped sample solution is held inside the porous base member 13, the SAW sensor 1 can inhibit the solution from evaporating.

Moreover, the SAW sensor 1 can allow the solution drop to reliably come into contact with a preliminarily-determined specified area of the reaction-region thin film 12, and accurate measurement is possible.

Furthermore, according to the SAW sensor 1, since solution does not directly drop on the piezoelectric element substrate 10, when the dropping of solution is carried out by a measurer, a dripping instrument such as a micropipette does not directly come into contact with the reaction-region thin film 12 (sensor surface), damage such as scratches on the sensor surface thereof thereby does not occur, and simple and accurate measurement is possible.

Additionally, since it is possible to hold the liquid on a surface reaction region, a problem does not occur in that the liquid is not held by the SAW sensor 1 as a result of vertically or horizontally disposing the SAW sensor or vibrating the SAW sensor or a problem also does not occur in that the liquid comes into contact with an analyte, after the liquid serving as an analyte is introduced thereinto.

On the other hand, a biosensor that is referred to as a lateral flow is known.

The lateral flow is a sensor that carries out an antigen-antibody reaction by an immunochromatography using an antibody that identifies a measuring object immobilized in advance and outputs a detection result of the antigen-antibody reaction as a color.

Consequently, it is necessary to immobilize a staining material on the antibody that identifies a measuring object, a processing of coloring or staining is required, and there is a problem in that simple measurement cannot be performed.

Furthermore, since determination of color is carried out by a visual check, there is also a problem in that accuracy of measurement cannot be sufficiently ensured.

According to the SAW sensor 1, a processing of coloring or staining is not necessary, which is required for the case of detecting an antigen by use of an immunochromatography serving as a method of detecting a general antigen.

As a result, it is possible to easily carry out measurement with a high level of accuracy.

Second Embodiment

Hereinafter, a second embodiment of the invention will be described in detail with reference to drawings.

Particularly, in the explanation of the embodiment described below, identical symbols are used for the elements which are identical to those of the drawings, and the explanations thereof are omitted here.

In the second embodiment, the case will be described where the porous base member 13 includes a layer that is formed of a substance having a filtering function and a function of a reaction field.

Figure 4A:
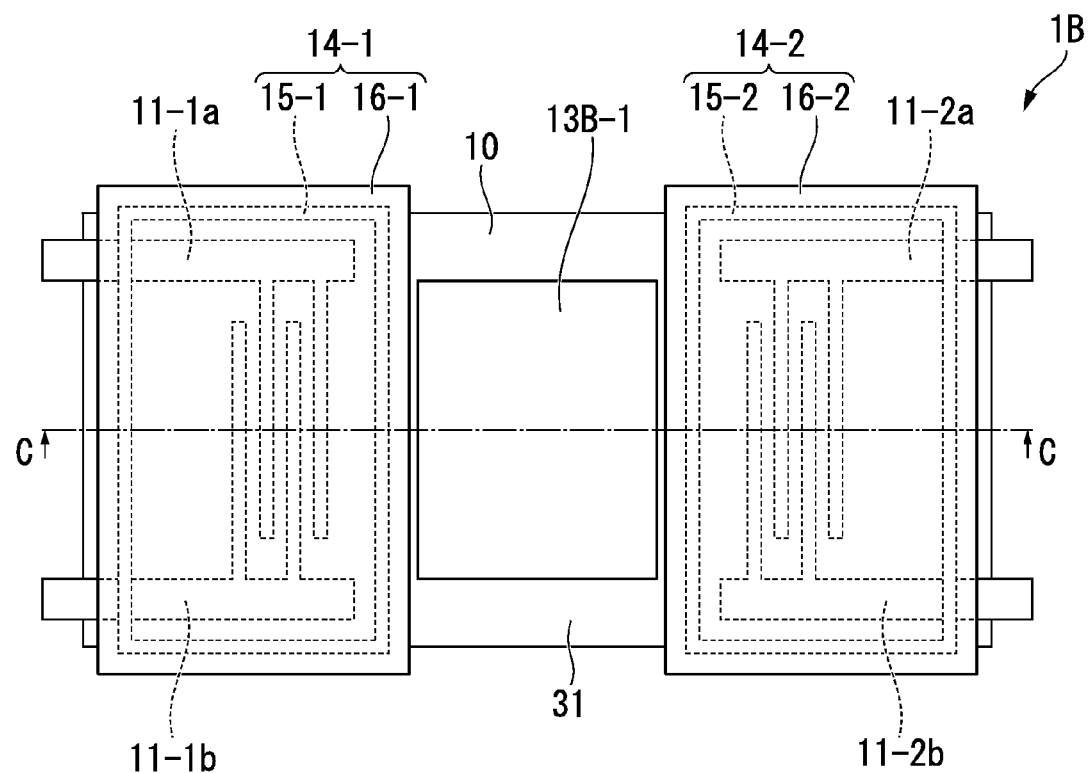
FIG. 4A is a schematic top view showing the configuration of a SAW sensor according to a second embodiment of the invention.
Figure 4B:
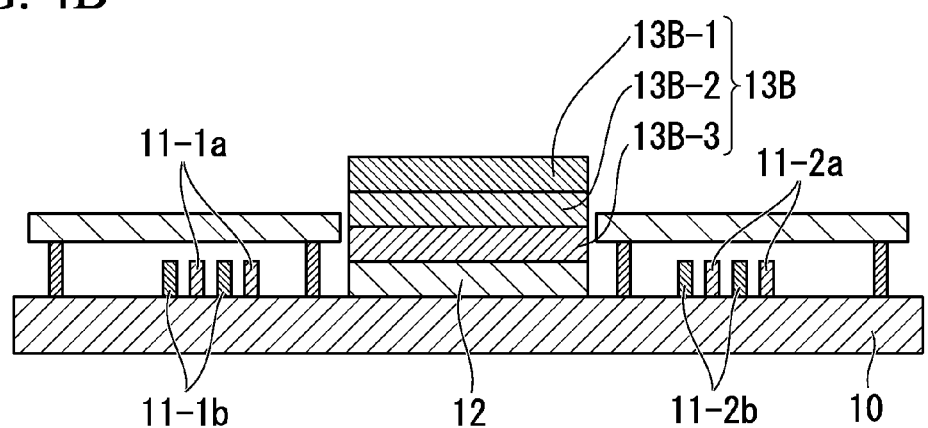
FIG. 4B is a schematic cross-sectional view showing the configuration of the SAW sensor according to the second embodiment of the invention.

FIGS. 4A and 4B are schematic views showing a configuration of a SAW sensor 1B according to a second embodiment.

In addition, in FIGS. 4A and 4B, identical symbols are used for the elements which are identical to those of FIGS. 1A, 1B, and 2, and the explanations thereof are omitted here.

FIG. 4A is a schematic top view showing the SAW sensor 1B.

FIG. 4B is a cross-sectional view showing the SAW sensor 1B as seen from the cross section C.

As shown in FIGS. 4A and 4B, the SAW sensor 1B is configured to include the piezoelectric element substrate 10, the IDT 11, the reaction-region thin film 12, the porous base member 13B, the sealing structure 14-1 and the sealing structure 14-2.

As shown in FIG. 4B, the porous base member 13B is configured to include a filter layer 13B-1, a reaction layer 13B-2, and a water retention layer 13B-3, and is arranged so that the filter layer 13B-1, the reaction layer 13B-2, and the water retention layer 13B-3 are stacked in layers on the reaction-region thin film 12 in order.

Particularly, in FIG. 4A, the water retention layer 13B-3 serving as an uppermost layer is shown and the case is shown in which the surface area of the porous base member 13B is different from that of FIGS. 1A and 1B and the same as the surface area of the reaction-region thin film 12.

As a matter of course, as long as a specified area is formed as mentioned above which has a surface area defined by the portion on which the porous base member 13 overlaps the reaction-region thin film 12, it is not necessary for both of them to have the same area.

The filter layer 13B-1 filters an unnecessary substance from the dropped sample solution.

The filter layer 13B-1 is a layer that is formed of a material such as cellulose or cellulose nitrate having micro pores.

A size of the micro pores of the filter layer 13B-1 is suitably selected depending on the unnecessary substance that is required to be removed.

A reactant that reacts with a sample is held by the reaction layer 13B-2 so as to be dispersed therein in advance.

The reaction layer 13B-2 is a layer that is formed of a material such as cellulose or cellulose nitrate having micro pores.

In the reaction layer 13B-2, the reactant, that passes through the filter layer 13B-1 and is transferred to the reaction layer 13B-2, reacts with the reactant, that is dispersed in the reaction layer 13B-2 in advance and reacts with a sample.

The product material that is generated in the reaction layer 13B-2 transfers to the water retention layer 13B-3 in accordance with solution infiltration.

In the case where an objective substance is, for example, an antigen, a first antibody is preliminarily dispersed in the reaction layer 13B-2.

The antigen antibody complex that is generated in the reaction layer 13B-2 transfers to the water retention layer 13B-3 in accordance with solution infiltration.

The water retention layer 13B-3 maintains the solution that is transported from the reaction layer 13B-2.

The water retention layer 13B-3 transfers the solution to the reaction-region thin film 12.

A material used to form the water retention layer is, for example, cellulose, cellulose nitrate, or the like having micro pores.

The water retention layer 13B-3 prevents transpiration of solution.

Additionally, the water retention layer 13B-3 transfers a reactant in solution to the reaction-region thin film 12, and holds it.

In the case where an objective substance is, for example, an antigen, the reaction-region thin film 12 preliminarily supports a second antibody.

The antigen-antibody complex including the antigen, that is transferred from the water retention layer 13B-3, and the first antibody, reacts with the second antibody on the reaction-region thin film 12.

As described above, in the second embodiment, the porous base member 13B is provided with the filter layer 13B-1 that removes other than a target body.

Because of this, since the SAW sensor 1B can prevent an unnecessary substance from reaching the reaction layer 13B-2, the reaction efficiency increases.

Moreover, since the SAW sensor 1B can prevent an unnecessary substance from reaching the reaction-region thin film 12, accurate measurement is possible.

Furthermore, the porous base member 13B is provided with the reaction layer 13B-2 including a substance that reacts with a sample.

For this reason, the mass of the sample to be detected becomes greater than that of the case where a sample independently adheres to the reaction-region thin film 12.

Therefore, as compared with the case where a sample independently adheres to the reaction-region thin film 12, the SAW sensor 1B can detect further significant signal variation.

As a result, accurate measurement is possible.

In other cases, the order in which the filter layer 13B-1 and the reaction layer 13B-2 are disposed may be reversed.

In other cases, one-layer film having functions of both reaction and water retention may be adopted instead of the reaction layer 13-B2 and the water retention layer 13-B3.

Third Embodiment

Hereinafter, a third embodiment of the invention will be described in detail with reference to drawings.

In the third embodiment, the case will be described where the reaction-region thin film 12 is constituted of two portions having electroconductive and insulation properties.

Figure 5A:
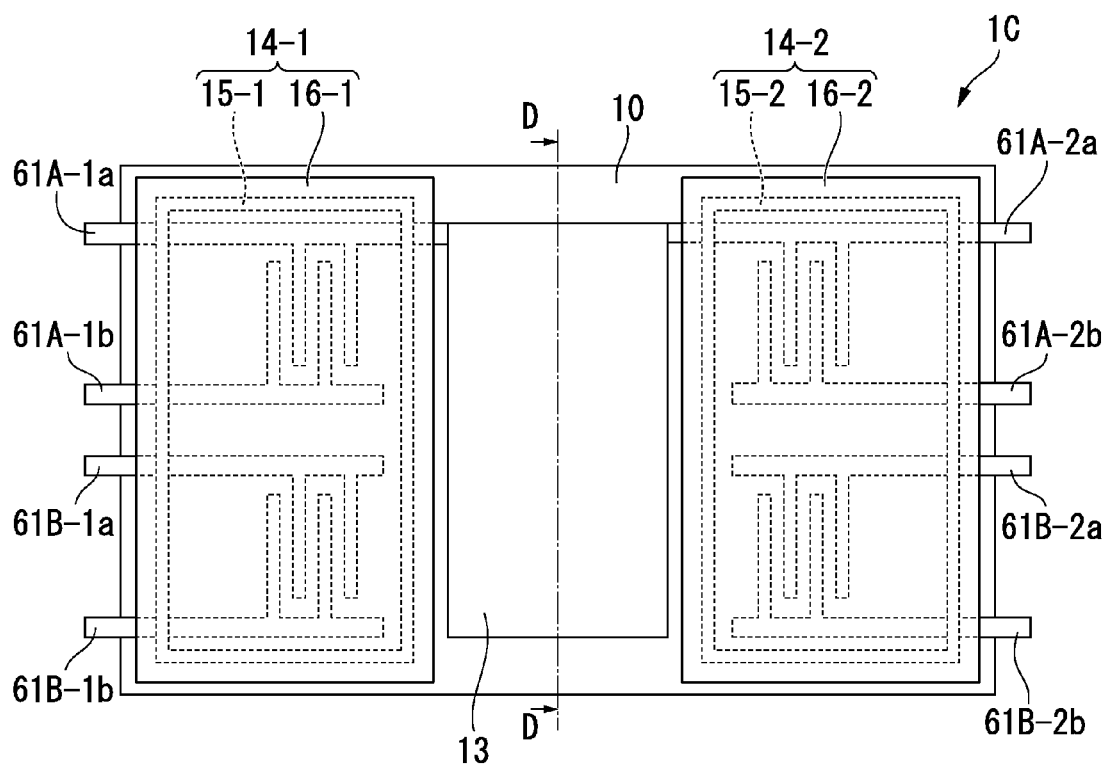
FIG. 5A is a schematic top view showing the configuration of a SAW sensor according to a third embodiment of the invention.
Figure 5B:
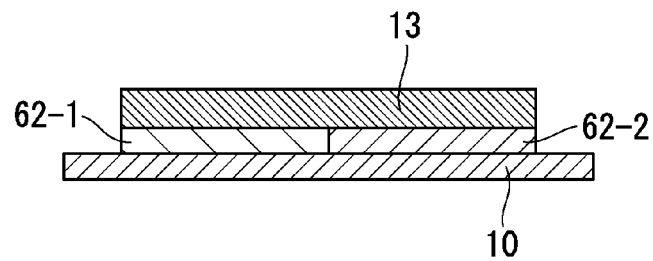
FIG. 5B is a schematic cross-sectional view showing the configuration of the SAW sensor according to the third embodiment of the invention.

FIGS. 5A and 5B are schematic views showing the configuration of a SAW sensor 1C according to the third embodiment.

In addition, in FIGS. 5A and 5B, identical symbols are used for the elements which are identical to those of FIGS. 1A, 1B, 2, 4A, and 4B, and the explanations thereof are omitted here.

FIG. 5A is a schematic view showing a configuration of the SAW sensor 1C as seen from the upper surface thereof.

FIG. 5B is a schematic view showing a configuration of the SAW sensor 1C as seen from the cross section D.

As shown in FIGS. 5A and 5B, the SAW sensor 1C is configured to include the piezoelectric element substrate 10, the porous base member 13, a transmission electrode 61A-1a, a transmission electrode 61A-1b, a reception electrode 61A-2a, a reception electrode 61A-2b (which are collectively referred to as IDT 61A), a transmission electrode 61B-1a, a transmission electrode 61B-1b, a reception electrode 61B-2a, a reception electrode 61B-2b (which are collectively referred to as IDT 61B), a short-circuiting reaction region 62-1, an open reaction region 62-2, the sealing structure 14-1, and the sealing structure 14-2.

The IDT 61A excites a SAW, that propagates along the region on which an electrically-short-circuited short-circuiting reaction region 62-1 is provided, and detects it.

The IDT 61B excites a SAW, that propagates along the region on which an electrically-opened open reaction region 62-2 is provided, and detects it.

As shown in FIG. 5B, the short-circuiting reaction region 62-1 is provided on the piezoelectric element substrate 10.

The short-circuiting reaction region 62-1 is a thin film made of a thin film having electroconductivity such as gold.

The short-circuiting reaction region 62-1 is electrically in contact with the IDT 61A-1a and the IDT 61A-2a which are electrically connected to the ground.

Additionally, the open reaction region 62-2 is provided on the piezoelectric element substrate 10 and is a region of the surface of the piezoelectric element substrate 10.

The short-circuiting reaction region 62-1 and the open reaction region 62-2 are arranged substantially parallel to a direction in which the IDT 61A and the IDT 61B are arranged.

The short-circuiting reaction region 62-1 and the open reaction region 62-2 are formed in a rectangle shape and are in contact with each other.

The total of the surface area of the short-circuiting reaction region 62-1 and the surface area of the open reaction region 62-2 is substantially the same as the surface area of the porous base member 13B.

As a matter of course, as long as a specified area is formed which has a surface area defined by the portion on which the porous base member 13 overlaps the short-circuiting reaction region 62-1 and the open reaction region 62-2 as mentioned above, both of them are not necessary to have the same area.

Moreover, the surface area of the short-circuiting reaction region 62-1 is substantially equal to the surface area of the open reaction region 62-2; however, they may be the same as each other or may be different from each other by a certain percentage of the surface area.

In addition, the reaction region is shown here as a rectangle shape; however, it is not necessary to limit the shape of the reaction region to this rectangle shape, and other shapes may be adopted.

A solution that drops on the porous base member 13 uniformly infiltrates on the top surfaces of the short-circuiting reaction region 62-1 and the open reaction region 62-2.

The surfaces of the short-circuiting reaction region 62-1 and the open reaction region 62-2 which face the porous base member 13 is uniformly wet with the sample solution.

Here, a transmission speed of the SAW that transmits the short-circuiting reaction region 62-1 varies depending on the density of a solution and the degree of viscosity thereof.

On the other hand, a transmission speed of the SAW that transmits the open reaction region 62-2 varies depending on the density of solution, the degree of viscosity, and electrical characteristics (relative permittivity and electrical conductivity).

The IDT 61A detects a transmission time of the SAW that transmits the short-circuiting reaction region 62-1.

On the other hand, the IDT 61B detects a transmission time of the SAW that transmits the open reaction region 62-2.

Therefore, a difference between the transmission time of the SAW that transmits the short-circuiting reaction region 62-1 and the transmission time of the SAW that transmits the open reaction region 62-2 represents a difference in electrical characteristics of the solution.

As stated above, according to the third embodiment, the SAW sensor 1C is provided with the open reaction region 62-2 that is not electrically connected to the IDT 61B and the short-circuiting reaction region 62-1 that is electrically connected to the IDT 61A.

Because of this, based on the difference between the transmission time of the SAW that transmits the short-circuiting reaction region 62-1 and the transmission time of the SAW that transmits the open reaction region 62-2, it is possible to individually detect the density, the degree of viscosity, and the electrical characteristics of solution that is dropped on the top surface of the porous base member 13.

Additionally, a difference in level, which is due to the thickness of the short-circuiting reaction region 62-1, is formed between the short-circuiting reaction region 62-1 and the open reaction region 62-2.

However, since the short-circuiting reaction region 62-1 is sufficiently thin, the porous base member 13 can maintain a contact between the short-circuiting reaction region 62-1 and the open reaction region 62-2, and does not affect the measurement of the SAW.

Fourth Embodiment

Hereinafter, a fourth embodiment of the invention will be described in detail with reference to drawings.

In the fourth embodiment, the case will be described where the SAW sensor 1D includes three measurement channels (channel A, channel B, and channel C) and a porous base member corresponding to the three measurement channels includes regions in which respective antibodies different from each other are distributed.

Figure 6:
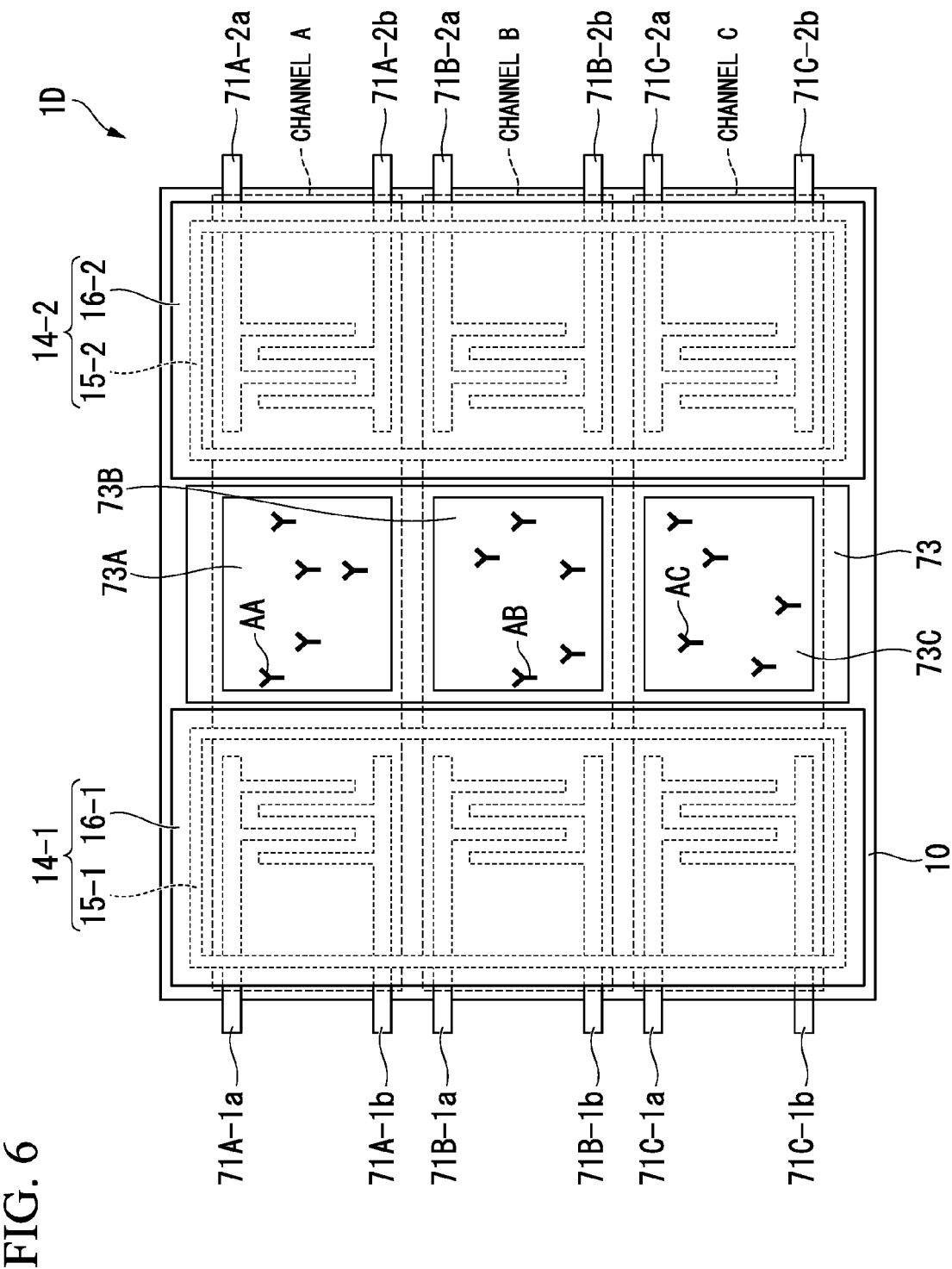
FIG. 6 is a schematic view showing a configuration of a SAW sensor according to a fourth embodiment of the invention.

FIG. 6 is a schematic view showing a configuration of the SAW sensor 1D according to the fourth embodiment.

In addition, in FIG. 6, identical symbols are used for the elements which are identical to those of FIGS. 1A, 1B, 2, 4A, 4B, 5A, and 5B, and the explanations thereof are omitted here.

As shown in FIG. 6, the SAW sensor 1D is configured to include the piezoelectric element substrate 10, a transmission electrode 71A-1a, a transmission electrode 71A-1b, a reception electrode 71A-2a, a reception electrode 71A-2b (collectively referred to as IDT 71A), a transmission electrode 71B-1a, a transmission electrode 71B-1b, a reception electrode 71B-2a, a reception electrode 71B-2b (collectively referred to as IDT 71B), a transmission electrode 71C-1a, a transmission electrode 71C-1b, a reception electrode 71C-2a, a reception electrode 71C-2b (collectively referred to as IDT 71C), the reaction-region thin film 12 (not shown in FIG. 6), a porous base member 73, the sealing structure 14-1, and the sealing structure 14-2.

The porous base member 73 is configured to include a region 73A, a region 73B, and a region 73C, which have respective primary antibodies that are different from each other and distributed therein.

The IDT 71A, the IDT 71B, and the IDT 71C generate SAWs which propagate through the channel A, the channel B, and the channel C and receive them, respectively.

When a solution drops on the top surface of the porous base member 73, the solution infiltrates into the inside of the porous base member 73.

The solution drop infiltrates into the region 73A of the porous base member 73 in which an antibody AA represented by reference letter AA is dispersed, the region 73B thereof in which an antibody AB represented by reference letter AB is dispersed, and the region 73C thereof in which an antibody AC represented by reference letter AC is dispersed.

Here, the region 73A, the region 73B, and the region 73C may be part of a common porous base member 73 or may be a base member that is newly provided on a common porous base member 73.

In the case where a plurality of kinds of antigens are contained in the solution that is dropped on the region 73A, the region 73B, and the region 73C, antigen-antibody combined bodies are generated at the respective portions in which antibodies corresponding to the respective antigens are dispersed.

The generated antigen-antibody combined bodies reach the top of the reaction-region thin film 12 due to diffusion.

The surface of the reaction-region thin film 12 supports second antibodies in advance which correspond to the respective the first antibodies dispersed in the region 73A, the region 73B, and the region 73C.

The second antibodies supported by the surface of the reaction-region thin film 12 capture the respective antigen-antibody complexes having masses which are different from each other in each of the channel A, the channel B, and the channel C.

As a result, transmission times of the SAW in the respective channels are different from each other.

The SAW sensor 1D shows a different transmission time for each channel.

As described above, according to the fourth embodiment, a plurality of electrode pairs that are constituted of the transmission electrode and the reception electrode is provided, and the porous base member includes the antibodies, that react with the respective kinds of antigen, between the paired electrodes of the IDT 71A, the IDT 71B, and the IDT 71C.

As a result, the SAW sensor 1D can simultaneously measure a plurality of different antigens.

Moreover, in the fourth embodiment, the number of the channels is three, but any number of the channels may be adopted.

In other cases, in the first to fourth embodiments, the piezoelectric element substrate 10 may be a substrate made of a substance exhibiting a piezoelectric effect such as lithium tantalate, lithium niobate, or lithium tetraborate.

Furthermore, even other than aluminum, other materials may be adopted as a material used to form the IDT as long as the material is a high conductive metal.

Also, in the aforementioned first to fourth embodiments, the reaction-region thin film is not limited to have a structure in which an antibody is disposed and may adopt a structure in which an antigen is disposed. As long as a reaction-region thin film is made of a material or a structure which specifically reacts with a body to be detected, the reaction-region thin film is not limited to the above-mentioned embodiment.

In addition, in the above-described first to fourth embodiments, the reaction-region thin film 12 supports an antibody and measures an antigen; and if it is not used to measure an antigen, it is not necessary to provide the reaction-region thin film 12.

Additionally, in the above-described first to fourth embodiments, a transmission electrode and a reception electrode are used; but, a transmission electrode may double with a function of a reception electrode by provision of a reflector of the SAW instead of a reception electrode.

Furthermore, an electrode structure of the IDT 11 is not limited to the structure shown in the drawings. Regarding the electrode structure, for example, where the wavelength of a surface acoustic wave is represented as $\lambda$, the width of an interdigitated array electrode may be $\lambda/4$ or $\lambda/8$, or an electrode structure may be a unidirectional electrode (FEUDT: Floating Electrode Uni Directional Transducer) or the like.

Fifth Embodiment

Hereinafter, an embodiment of the invention will be described in detail with reference to drawings.

In each embodiment described below, identical symbols are used for the elements which are identical to those described above, and the explanations thereof are omitted here.

Figure 7:
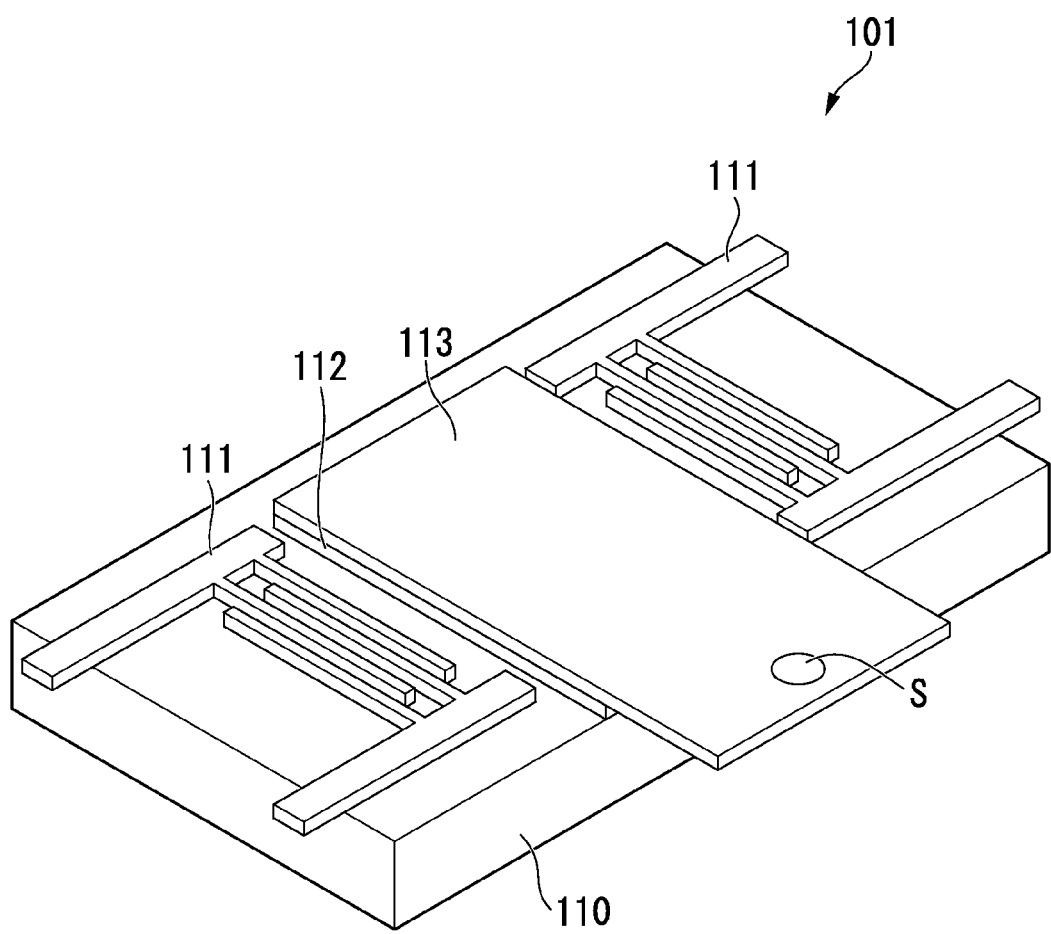
FIG. 7 is a schematic perspective view showing a SAW sensor according to a fifth embodiment of the invention.

FIG. 7 is a schematic perspective view showing a SAW sensor 101 according to a fifth embodiment.

As shown in FIG. 7, the SAW sensor 101 (surface acoustic wave sensor) is configured to include a piezoelectric element substrate 110 (piezo element), the IDT 111, a reaction-region thin film 112, and a porous base member 113.

In each embodiment described below, identical symbols are used for the elements which are identical to those described above, and the explanations thereof are omitted here.

The piezoelectric element substrate 110 is a substrate that propagates a SAW.

The piezoelectric element substrate 110 is a quartz substrate.

The IDT 111 (Inter Digital Transducer) is an electrode formed on the piezoelectric element substrate 110.

The IDT 111 is a comb-shaped electrode.

The IDT 111 is a pair of facing electrodes.

The IDT 111 is configured of an aluminum thin film.

The reaction-region thin film 112 is a thin film that is produced by vapor deposition of gold.

The reaction-region thin film 112 is a thin film having a surface on which an antibody is supported.

The reaction-region thin film 112 is formed on the piezoelectric element substrate 110 and on the region between the paired IDTs 111 that are provided on the piezoelectric element substrate 110 so as to face each other.

The porous base member 113 is a base member that is provided to be in contact with the reaction-region thin film 112.

The porous base member 113 is made of a substance such as cellulose nitrate.

The porous base member 113 is fixed so as to completely cover the reaction-region thin film 112 and so as not to come into contact with the IDT 111.

For example, the porous base member 113 is fixed by adhesively attaching the external four corners of the reaction-region thin film 112 thereto.

The porous base member 113 holds solution that drops thereon and allows the solution to infiltrate into the inside thereof and the surface thereof.

The region represented by reference letter S is an example of a region on which a solution drops.

The porous base member 113 transfers the solution, that dropped on the region represented by reference letter S, to the inside of the porous base member 113 and the surface of the reaction-region thin film 112 due to a capillary phenomenon, and holds it.

That is, the SAW sensor 101 holds the solution drop inside the porous base member 113 and thereon.

Therefore, it does not make the IDT 111 wet.

For this reason, the SAW sensor 101 can measure the solution without using a sealing structure.

As a result, it is possible to reduce manufacturing costs.

Figure 8A:
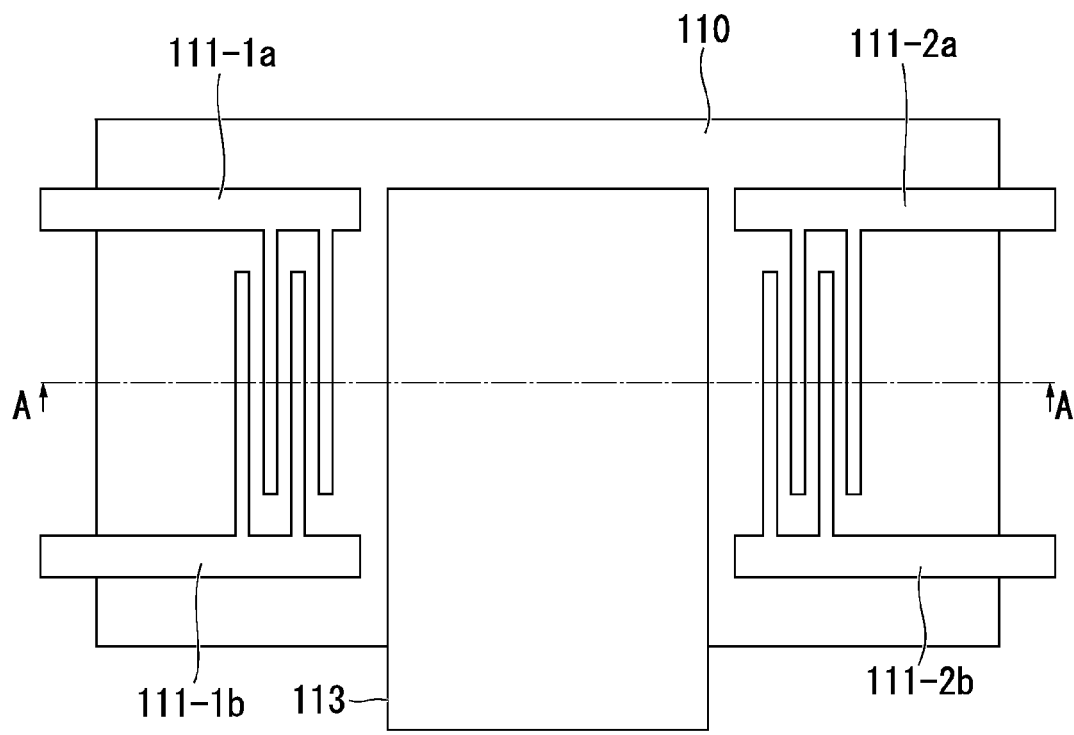
FIG. 8A is a schematic top view showing the SAW sensor according to the fifth embodiment of the invention.
Figure 8B:
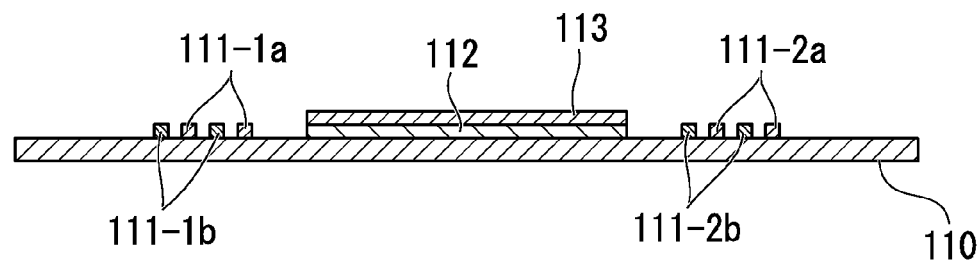
FIG. 8B is a schematic cross-sectional view showing the SAW sensor according to the fifth embodiment of the invention.

FIGS. 8A and 8B are schematic views showing the SAW sensor according to the fifth embodiment.

FIG. 8A is a schematic top view showing the SAW sensor 101.

Additionally, FIG. 8B is a schematic cross-sectional view showing the SAW sensor 101 as seen from the cutting plane A.

The IDT 111 provided on the SAW sensor 101 is configured to include transmission electrodes 111-1a and 111-1b that converts an electrical signal into a SAW and reception electrodes 111-2a and 111-2b that convert a SAW into an electrical signal.

A burst signal serving as a transmitting signal is input to the transmission electrodes 111-1a and 111-1b from a burst circuit 22 which will be described later.

The transmission electrodes 111-1a and 111-1b excite a SAW corresponding to the input burst signal on the surface of the piezoelectric element substrate 110.

The reception electrodes 111-2a and 111-2b convert the SAW that propagated along the surface of the piezoelectric element substrate 110 into an electrical signal.

The reception electrodes 111-2a and 111-2b output the received electrical signal (referred to as a detection signal) to a phase-amplitude detecting circuit 23 which will be described later.

FIG. 3 is a schematic block diagram illustrating the sense circuit 20 of the SAW sensor 101.

As shown in FIG. 3, the sense circuit 20 is configured to include the SAW sensor 101, an alternating-current signal source 21, the burst circuit 22, the phase-amplitude detecting circuit 23, and a PC 24 (Personal Computer).

Here, the period of the burst signal is set to be longer than a time required for propagation of the SAW from the transmission electrodes 111-1a and 111-1b (FIGS. 8A and 8B) to the reception electrodes 111-2a and 111-2b of the surface of the piezoelectric element substrate 110.

The burst circuit 22 outputs the generated burst signal to the SAW sensor 101 and the phase-amplitude detecting circuit 23.

In other cases, in the case where a disturbing signal such as noise including a direct wave, other bulk wave, or the like with the exception of a main signal included in the signal output from the SAW sensor 101 is sufficiently low, the burst circuit 22 is not necessary, and a continuous wave may be adopted.

Based on a detection signal input from the sensor 101 and the burst signal input from the burst circuit 22, the phase-amplitude detecting circuit 23 calculates a phase variation and an amplitude change which are associated with a propagation time that is a time required for propagation of the SAW on the piezoelectric element substrate 110.

Specifically, the phase-amplitude detecting circuit 23 detects a phase variation and attenuation of amplitude which is associated with a required time (referred to as a delay time) between the inputting of the burst signal and the inputting of the detection signal.

The phase-amplitude detecting circuit 23 outputs a phase variation and an amplitude change, which is due to the detected delay time, to the PC 24.

Based on the phase variation and the amplitude change which are input from the phase-amplitude detecting circuit 23, the PC 24 determines the amount of an antigen in a solution that were specifically-reacted with an antibody on the surface and displays the determination result.

Here, the phase variation and the amplitude change of the SAW will be described.

The SAW is an acoustic wave that concentrates in the vicinity of the surface of the piezoelectric element substrate 110 (the position close to the surface) and propagates.

When a substance is absorbed onto the top surface of the piezoelectric element substrate 110, the mass per unit volume and the degree of viscosity of the top surface thereof vary.

As a result, the propagation velocity and amplitude of the SAW vary.

For this reason, the phase variation and the amplitude change which are associated with the delay time of the SAW vary.

In the fifth embodiment, an antigen that is contained in solution is measured utilizing the phase and the amplitude change of the SAW.

Specifically, at first, a measurer makes the top of the reaction-region thin film 112 wet with the solvent, and measures the phase variation which is associated with a propagation time of the SAW, next, drops the solution containing an antigen thereon, and measures the phase variation and the amplitude change (blank test).

A difference between the propagation time corresponding to the solvent and the propagation time corresponding to the solution is a variation in phase which is caused by an antigen antibody complex that is generated in the reaction-region thin film 112 due to an antigen-antibody reaction.

The PC 24 measures the antigen contained in the solution based on the phase variation, and similarly, the amplitude change is measured.

In other cases, if the phase variation of the SAW in the solvent to be used is determined in advance, the measurer does not need to measure a phase variation of the SAW in the solvent.

Furthermore, even in the case where the propagation time of the SAW in the solvent to be used is not determined in advance, the PC 24 may determine an amount of and the kind of antigen in solution with reference to the propagation time and the amplitude which are immediately after dropping of solution containing an antigen as a result of obtaining a difference between subsequent changes based thereon, and also can display the determination result.

In the SAW sensor 101, the solution that is transported to the inside of the porous base member 113 makes a specified surface area of the reaction-region thin film 112 wet.

Here, the specified surface area means a surface area defined by the portion on which the porous base member 113 overlaps the reaction-region thin film 112.

The antigen in solution reacts with the antibody supported on the reaction-region thin film 112 and generates an antigen antibody complex on the reaction-region thin film 112.

In the reaction-region thin film 112, as a result of dropping a liquid sample including an antigen on the top surface thereof, an antigen-antibody reaction occurs between the antibody that is supported on the reaction-region thin film 112 and the antigen of the liquid sample.

Consequently, an antigen antibody complex in which the antibody that is supported on the reaction-region thin film 112 and the antigen are combined is produced on the reaction-region thin film 112.

In other cases, even other than gold, various materials may be adopted as a material used to form the reaction-region thin film 112 as long as the material can support an antibody.

Additionally, as shown in FIG. 7, since the porous base member 113 is larger than the reaction-region thin film 112, it protrudes from the reaction-region thin film 112.

The measurer drops a solution on the protrusion region S.

In other cases, the porous base member 113 does not necessarily protrude from the reaction-region thin film 112 as shown in the drawings.

In this case, the porous base member 113 is only necessary to be disposed so as to cover a fixed region of the reaction-region thin film 112 which is determined in advance.

As described above, the fifth embodiment includes: the piezoelectric element substrate 110 that propagates a surface acoustic wave; the transmission electrodes 111-1a and 111-1b that carries out conversion of the electrical signal into the surface acoustic wave; the reception electrodes 111-2a and 111-2b that carries out conversion of the surface acoustic wave into the electrical signal; and the porous base member 113 that comes into contact with the surface of the propagation path and holds the solution.

Consequently, in the fifth embodiment, since the SAW sensor 101 does not have a structure that seals the transmission electrodes 111-1a and 111-1b and the reception electrodes 111-2a and 111-2b, it is possible to reduce the manufacturing cost thereof.

Moreover, since a dropped sample solution is held inside the porous base member 113, the SAW sensor 101 can inhibit the solution from evaporating.

Also, the SAW sensor 101 can allow the solution drop to reliably come into contact with a preliminarily-determined specified area of the reaction-region thin film 112, and accurate measurement is possible.

Additionally, the SAW sensor 101 can hold the liquid on a surface reaction region, a problem which is due to vertically or horizontally disposing the sensor chip, vibrating the SAW sensor, or the like, does not occur, or a problem of a liquid coming into contact with an analyte again does not occur, after the liquid serving as an analyte is introduced thereinto.

Furthermore, according to the SAW sensor 101, since a solution does not directly drop on the piezoelectric element substrate 110, when the dropping of solution is carried out by a measurer, damage such as scratches on the sensor surface thereof does not occur, and simple and accurate measurement is possible.

In the SAW sensor 101, a processing of coloring or staining is not necessary, which is required for a case where an antigen is detected by use of immunochromatography serving as a method of detecting a general antigen.

As a result, it is possible to easily carry out measurement.

Sixth Embodiment

Hereinafter, a sixth embodiment of the invention will be described in detail with reference to drawings.

Figure 9A:
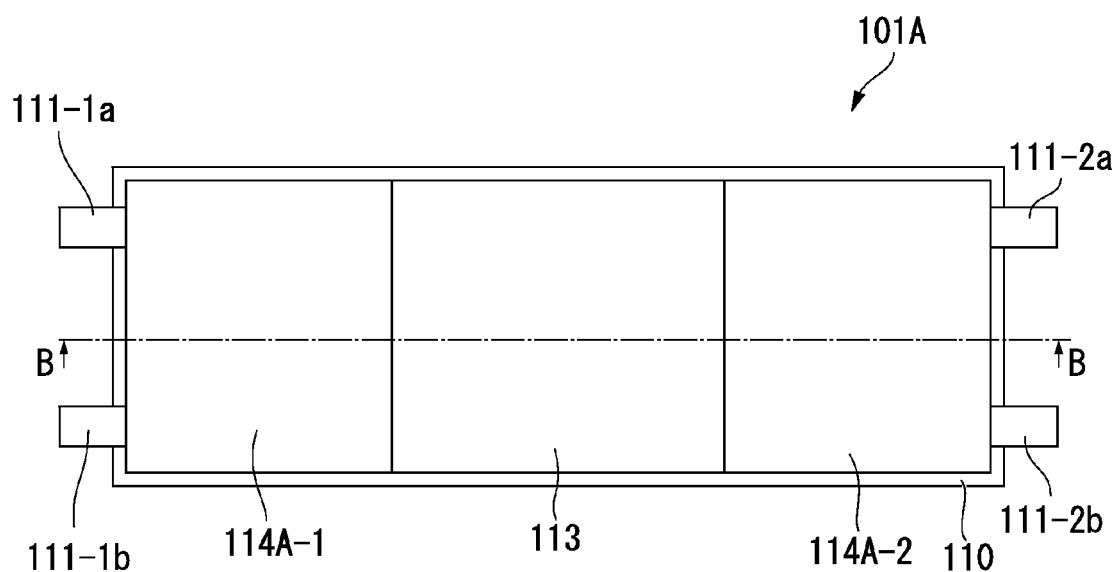
FIG. 9A is a schematic top view showing a configuration of a SAW sensor according to a sixth embodiment of the invention.
Figure 9B:
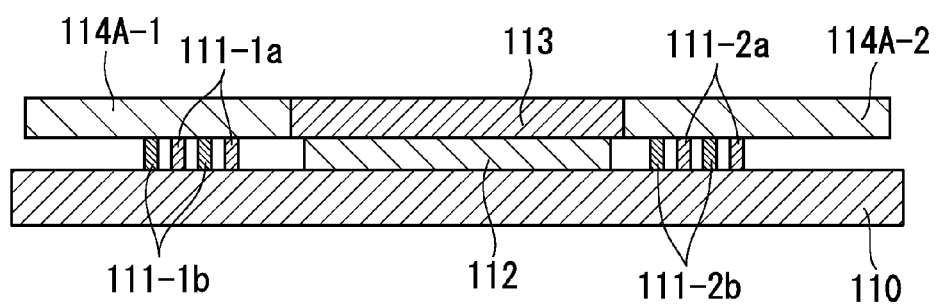
FIG. 9B is a schematic cross-sectional view showing the configuration of the SAW sensor according to the sixth embodiment of the invention.

FIGS. 9A and 9B are schematic views showing the SAW sensor 101A according to the sixth embodiment.

FIG. 9A is a schematic top view showing the SAW sensor 101A.

FIG. 9B is a cross-sectional view showing the SAW sensor 101A as seen from the cross section B.

As shown in FIGS. 9A and 9B, the SAW sensor 101A is configured to include the piezoelectric element substrate 110, the transmission electrodes 111-1a and 111-1b, the reception electrodes 111-2a and 111-2b (the transmission electrodes 111-1a and 111-1b and the reception electrodes 111-2a and 111-2b are collectively referred to as IDT 111), the reaction-region thin film 112, the porous base member 113 and a hydrophobic base members 114A-1 and 114A-2.

In the sixth embodiment, the case will be described where the porous base member 113 is connected to the hydrophobic base members 114A-1 and 114A-2 by adhesion or the like, the hydrophobic base members 114A-1 and 114A-2 are arranged so as to cover the upper surface of the IDT 111.

The hydrophobic base members 114A-1 and 114A-2 are made of a substance of a material that does not allow a solution to infiltrate thereinto.

Here, a material that does not allow a solution to infiltrate thereinto is, for example, plastic (polyethylene or the like).

As shown in the drawings, the hydrophobic base members 114A-1 and 114A-2 are connected to respective both opposed sides of the IDT 111 side of the porous base member 113 (which is disposed at the position close to the IDT 111).

The sample solution that dropped on the porous base member 113 infiltrates into the entire porous base member 113 due to a capillary phenomenon.

On the other hand, since the solution does not infiltrate into the hydrophobic base members 114A-1 and 114A-2, the IDT 111 does not become wet with a solution.

Moreover, the porous base member 113 is fixed by adhesively attaching the four corners of the reaction-region thin film 112 thereto.

As stated above, in the sixth embodiment, the portions of the hydrophobic base members 114A-1 and 114A-2, which come into contact with the transmission electrodes 111-1a and 111-1b and the reception electrodes 111-2a and 111-2b, have hydrophobicity.

For this reason, in the SAW sensor 101A, the transmission electrodes 111-1a and 111-1b and the reception electrodes 111-2a and 111-2b do not become wet with solution, and accurate measurement is possible.

Furthermore, since the surfaces of the transmission electrodes 111-1a and 111-1b and the reception electrodes 111-2a and 111-2b are covered with the hydrophobic base members 114A-1 and 114A-2, it is possible to protect the transmission electrodes 111-1a and 111-1b and the reception electrodes 111-2a and 111-2b.

Seventh Embodiment

Hereinafter, a seventh embodiment of the invention will be described in detail with reference to drawings.

In the seventh embodiment, the case will be described where the porous base member 113 includes a layer made of a substance having a filtering function and a function as a reaction field.

Figure 10A:
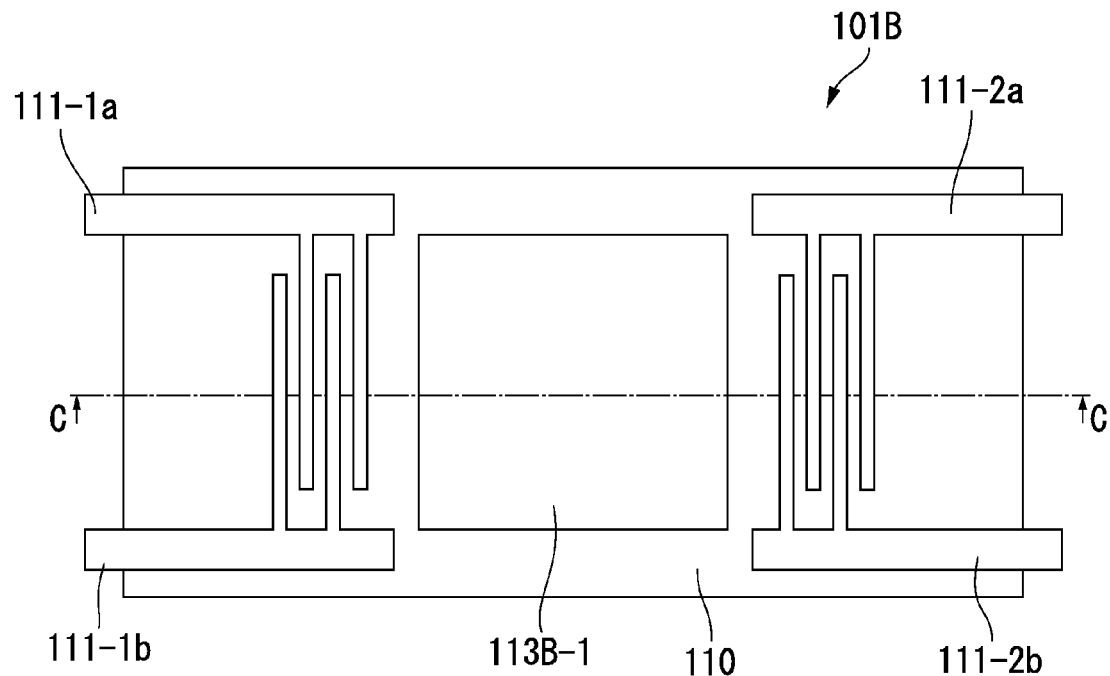
FIG. 10A is a schematic top view showing a configuration of a SAW sensor according to a seventh embodiment of the invention.
Figure 10B:
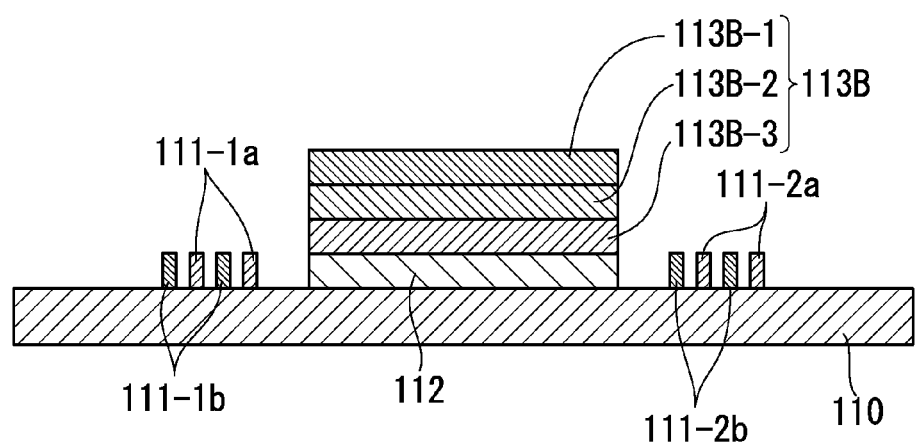
FIG. 10B is a schematic cross-sectional view showing the configuration of the SAW sensor according to the seventh embodiment of the invention.

FIGS. 10A and 10B are schematic views showing a configuration of the SAW sensor 101B according to the seventh embodiment.

FIG. 10A is a schematic top view showing the SAW sensor 101B.

FIG. 10B is a cross-sectional view showing the SAW sensor 101B as seen from the cross section C.

As shown in FIGS. 10A and 10B, the SAW sensor 101B is configured to include the piezoelectric element substrate 110, the IDT 111, the reaction-region thin film 112, and the porous base member 113B.

The porous base member 113B is configured to include a filter layer 113B-1, a reaction layer 113B-2, and a water retention layer 113B-3.

The filter layer 113B-1 filters an unnecessary substance from the dropped sample solution.

The filter layer 113B-1 is a layer that is formed of a material such as cellulose or cellulose nitrate having micro pores.

A size of the micro pores of the filter layer 113B-1 is suitably selected depending on an unnecessary substance that is required to be removed.

A reactant that reacts with a sample is held by the reaction layer 113B-2 so as to be dispersed therein in advance.

The reaction layer 113B-2 is a layer that is formed of a material such as cellulose or cellulose nitrate having micro pores.

In the reaction layer 113B-2, the reactant, that passes through the filter layer 113B-1 and is transferred to the reaction layer 113B-2, reacts with the reactant that is dispersed in the reaction layer 113B-2 in advance and reacts with a sample.

The product material that is generated in the reaction layer 113B-2 transfers to the water retention layer 113B-3 in accordance with solution infiltration.

In the case where an objective substance is, for example, an antigen, a first antibody is preliminarily dispersed in the reaction layer 113B-2.

The antigen antibody complex that is generated in the reaction layer 113B-2 transfers to the water retention layer 113B-3 in accordance with solution infiltration.

The water retention layer 113B-3 maintains the solution that is transported from the reaction layer 113B-2.

The water retention layer 113B-3 transfers the solution to the reaction-region thin film 112.

A material used to form the water retention layer is, for example, cellulose, cellulose nitrate, or the like having micro pores.

The water retention layer 113B-3 prevents transpiration of solution.

Additionally, the water retention layer 113B-3 transfers a reactant in solution to the reaction-region thin film 112.

In the case where an objective substance is, for example, an antigen, the reaction-region thin film 112 preliminarily supports a second antibody.

The antigen-antibody complex including the antigen, that is transferred from the water retention layer 113B-3, and the first antibody, reacts with the second antibody on the reaction-region thin film 112.

As described above, in the seventh embodiment, the porous base member 113B is provided with the filter layer 113B-1 that removes other than a target body.

Because of this, since the SAW sensor 101B can prevent an unnecessary substance from reaching the reaction layer 113B-2, the reaction efficiency increases.

Moreover, since the SAW sensor 101B can prevent an unnecessary substance from reaching the reaction-region thin film 112, accurate measurement is possible.

Furthermore, the porous base member 113B is provided with the reaction layer 113B-2 including a substance that reacts with a sample.

For this reason, the mass of the sample to be detected becomes greater than that of the case where a sample independently adheres to the reaction-region thin film 112.

Therefore, as compared with the case where a sample independently adheres to the reaction-region thin film 112, the SAW sensor 101B can detect further significant signal variation.

As a result, accurate measurement is possible.

In other cases, the order in which the filter layer 113B-1 and the reaction layer 113B-2 are disposed may be reversed.

In other cases, one-layer film having functions of both reaction and water retention may be adopted instead of the reaction layer 113-B2 and the water retention layer 113-B3.

Eighth Embodiment

Hereinafter, an eighth embodiment of the invention will be described in detail with reference to drawings.

In the eighth embodiment, the case will be described where the reaction-region thin film 112 is constituted of two portions having electroconductive and insulation properties.

Figure 11A:
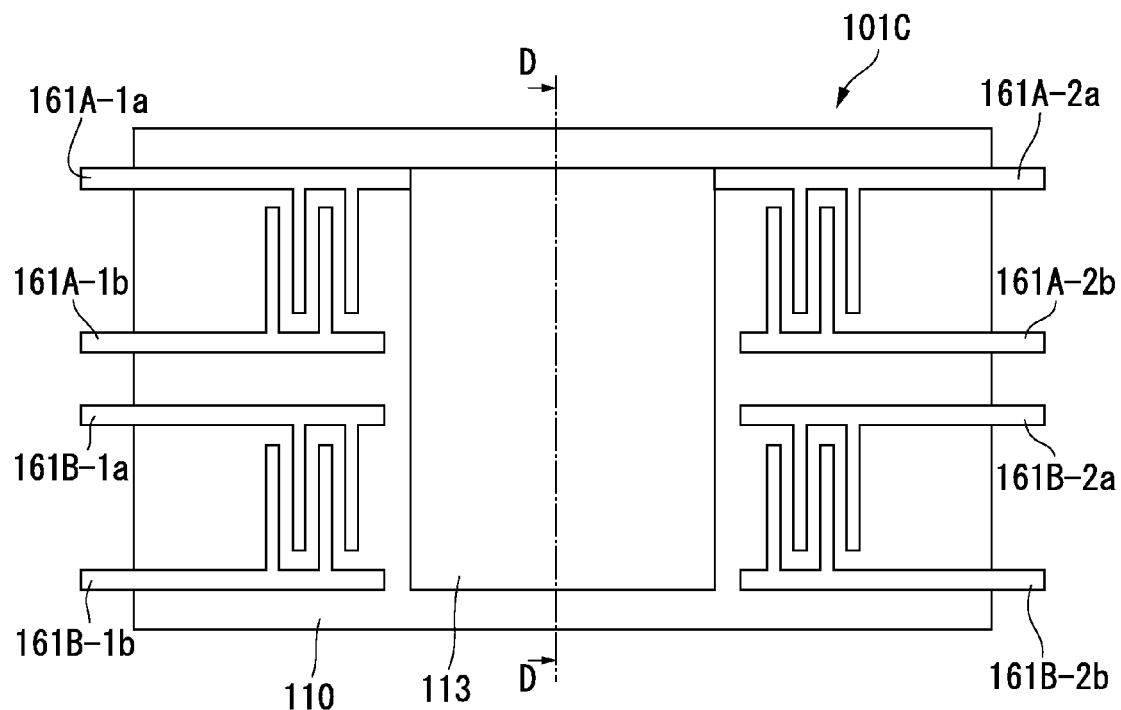
FIG. 11A is a schematic top view showing the configuration of a SAW sensor according to an eighth embodiment of the invention.
Figure 11B:
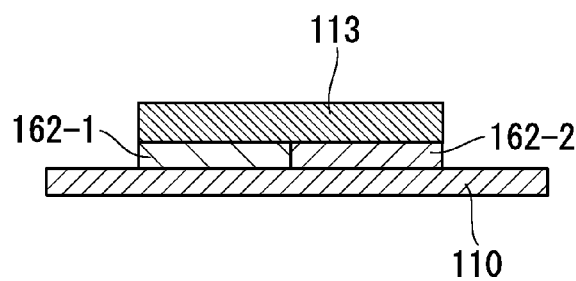
FIG. 11B is a schematic cross-sectional view showing the configuration of the SAW sensor according to the eighth embodiment of the invention.

FIGS. 11A and 11B are schematic views showing a configuration of a SAW sensor 101C according to the eighth embodiment.

FIG. 11A is a schematic view showing a configuration of the SAW sensor 101C as seen from the upper surface thereof.

FIG. 11B is a schematic view showing a configuration of the SAW sensor 101C as seen from the cross section D.

As shown in FIGS. 11A and 11B, the SAW sensor 101C is configured to include the piezoelectric element substrate 110, the porous base member 113, the IDT 161A-1a, 161A-1b, 161A-2a, 161A-2b (which are collectively referred to as IDT 161A), the IDT 161B-1a, 161B-1b, 161B-2a, 161B-2b (which are collectively referred to as IDT 161B), a short-circuiting reaction region (second portion)162-1, and an open reaction region (first portion)162-2.

The IDT 161A excites a SAW, that propagates along the region on which an electrically-short-circuited short-circuiting reaction region 162-1 is provided, and detects it.

The IDT 161B excites a SAW, that propagates along the region on which an electrically-opened open reaction region 162-2 is provided, and detects it.

The open reaction region 162-2 is provided on the piezoelectric element substrate 110 and is a surface of the piezoelectric element substrate 110.

The short-circuiting reaction region 162-1 is a thin film made of a thin film having electroconductivity such as gold.

The short-circuiting reaction region 162-1 is electrically in contact with the IDT 161A-1a and the IDT 161A-2a which are electrically connected to the ground.

A solution that drops on the porous base member 113 uniformly infiltrates the top surfaces of the short-circuiting reaction region 162-1 and the open reaction region 162-2.

The surfaces of the short-circuiting reaction region 162-1 and the open reaction region 162-2 which face the porous base member 113 is uniformly wet with the sample solution.

Here, the transmission speed of the SAW that transmits the short-circuiting reaction region 162-1 varies depending on the density of solution and the degree of viscosity thereof.

On the other hand, a transmission speed of the SAW that transmits the open reaction region 162-2 varies depending on the density of solution, the degree of viscosity, and the electrical characteristics (relative permittivity and electrical conductivity).

The IDT 161A determines the transmission time of the SAW that transmits the short-circuiting reaction region 162-1.

On the other hand, the IDT 161B detects a transmission time of the SAW that transmits the open reaction region 162-2.

Therefore, the difference between the transmission time of the SAW that transmits the short-circuiting reaction region 162-1 and the transmission time of the SAW that transmits the open reaction region 162-2 represents the difference in electrical characteristics of a solution.

As stated above, according to the eighth embodiment, the SAW sensor 101C is provided with the open reaction region 162-2 that is not electrically connected to the IDT 161B and the short-circuiting reaction region 162-1 that is electrically connected to the IDT 161A.

Because of this, based on a difference between a transmission time of the SAW that transmits the short-circuiting reaction region 162-1 and the transmission time of the SAW that transmits the open reaction region 162-2, it is possible to individually detect the density, the degree of viscosity, and the electrical characteristics of a solution that is dropped on the top surface of the porous base member 113.

Additionally, the difference in level which is due to the thickness of the short-circuiting reaction region 162-1 occurs between the short-circuiting reaction region 162-1 and the open reaction region 162-2.

However, since the short-circuiting reaction region 162-1 is sufficiently thin, the porous base member 113 can maintain a contact between the short-circuiting reaction region 162-1 and the open reaction region 162-2, there is no influence to measure the SAW.

Ninth Embodiment

Hereinafter, a ninth embodiment of the invention will be described in detail with reference to drawings.

In the ninth embodiment, the case will be described where the SAW sensor 101D includes three measurement channels (channel A, channel B, and channel C) and a porous base member 172A, 172B, and 172C corresponding to the three measurement channels includes portions in which respective antibodies different from each other are distributed.

Figure 12:
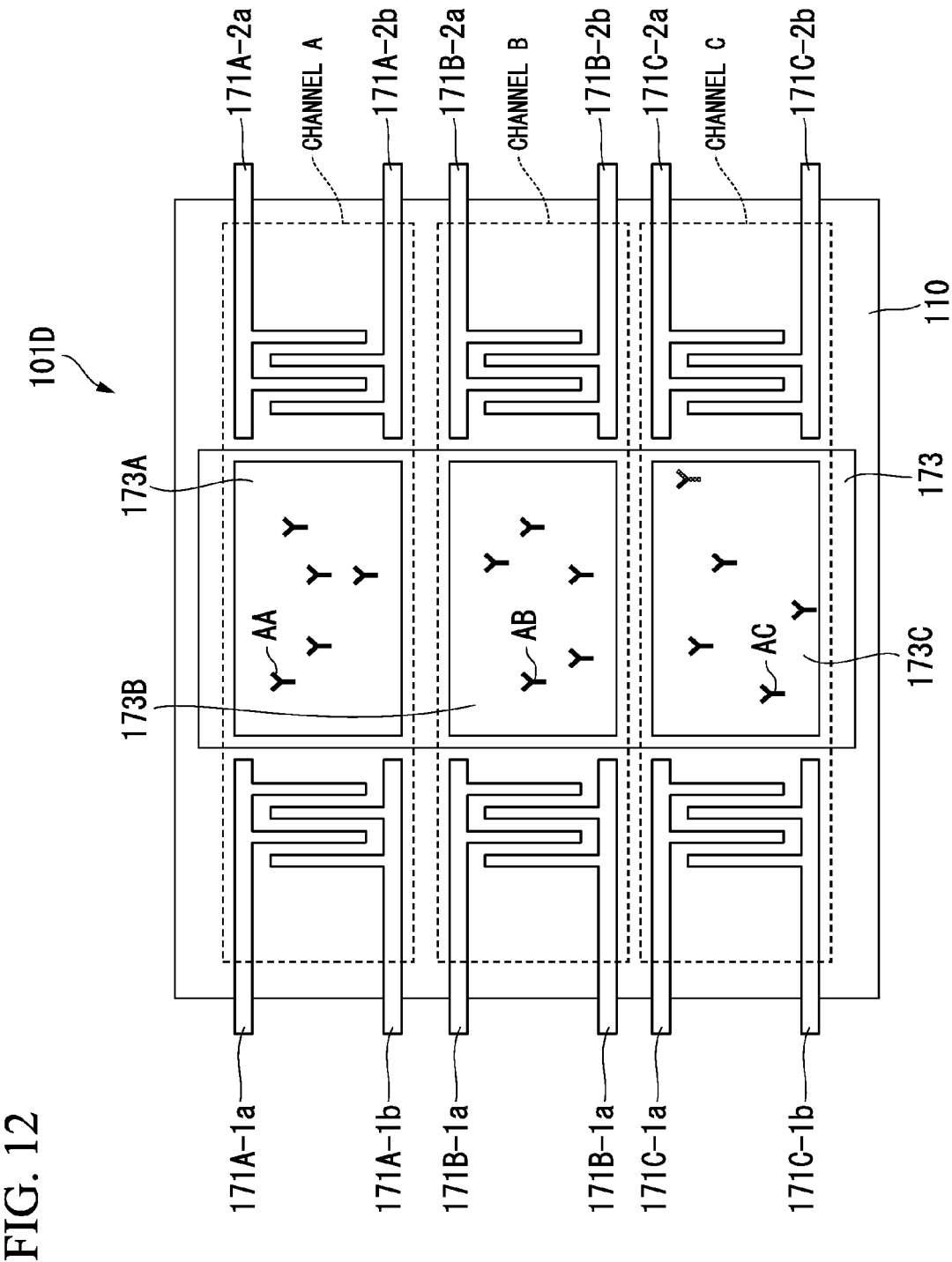
FIG. 12 is a schematic view showing a configuration of a SAW sensor according to a ninth embodiment of the invention.

FIG. 12 is a schematic view showing a configuration of the SAW sensor 101D according to the ninth embodiment.

As shown in FIG. 12, the SAW sensor 101D is configured to include the piezoelectric element substrate 110, IDTs 171A-1a, 171A-1b, 171A-2a, and 171A-2b (collectively referred to as IDT 171A), IDTs 171B-1a, 171B-1b, 171B-2a, and 171B-2b (collectively referred to as IDT 171B), IDTs 171C-1a, 171C-1b, 171C-2a, and 171C-2b (collectively referred to as IDT 171C), the reaction-region thin film 112 (not shown in the figure), and a porous base member 173.

The porous base member 173 is configured to include regions 173A, 173B, and 173C, which have respective primary antibodies that are different from each other and distributed therein.

The IDT 171A, the IDT 171B, and the IDT 171C generate SAWs which propagate through the channel A, the channel B, and the channel C and receive them, respectively.

When solution drops on the top surface of the porous base member 173, the solution infiltrates into the inside of the porous base member 173.

The solution drop infiltrates into the region 173A of the porous base member 173 in which an antibody AA represented by reference letter AA is dispersed, the region 173B thereof in which an antibody AB represented by reference letter AB is dispersed, and the region 173C thereof in which an antibody AC represented by reference letter AC is dispersed.

Here, the regions 173A, 173B, and 173C may be part of a common porous base member 173 or may be a base member that is newly provided on a common porous base member 173.

In the case where a plurality of kinds of antigens are contained in the solution that is dropped on the regions 173A, 173B, and 173C, antigen-antibody combined bodies are generated at the respective portions in which antibodies corresponding to the respective antigens are dispersed.

The generated antigen-antibody combined bodies reach the top of the reaction-region thin film 112 due to diffusion.

The surface of the reaction-region thin film 112 supports second antibodies in advance which correspond to the respective the first antibodies dispersed in the regions 173A, 173B, and 173C.

The second antibodies supported by the surface of the reaction-region thin film 112 capture the respective antigen-antibody complexes having masses which are different from each other in each of the channel A, the channel B, and the channel C.

As a result, transmission times of the SAW in the respective channels are different from each other.

The SAW sensor 101D shows a different transmission time for each channel.

As described above, according to the ninth embodiment, a plurality of electrode pairs that are constituted of the transmission electrode and the reception electrode is provided, and the porous base member includes the antibodies, that react with the respective kinds of antigen, between the paired electrodes of the IDT 171A, the IDT 171B, and the IDT 171C.

As a result, the SAW sensor 101D can simultaneously measure a plurality of different antigens.

Moreover, in the ninth embodiment, the number of the channels is three, but any number of the channels may be adopted.

In other cases, in the fifth to ninth embodiments, the piezoelectric element substrate 110 may be a substrate made of a substance exhibiting a piezoelectric effect such as lithium tantalate, lithium niobate, or lithium tetraborate.

Furthermore, in the above-described fifth to ninth embodiments, even other than aluminum, other materials may be adopted as a material used to form the IDT 111 (including 161A, 171A, 171B, and 171C) as long as the material is a high conductive metal.

Also, in the aforementioned fifth to ninth embodiments, the reaction-region thin film is not limited to have a structure in which an antibody is disposed and may adopt a structure in which an antigen is disposed. As long as a reaction-region thin film is made of a material or a structure which specifically reacts with a body to be detected, the reaction-region thin film is not limited to the above-mentioned embodiment.

In addition, in the above-described fifth to ninth embodiments, the reaction-region thin film 112 supports an antibody and measures an antigen; and if it is not used to measure an antigen, it is not necessary to provide the reaction-region thin film 112.

Additionally, in the above-described fifth to ninth embodiments, transmission electrodes 111-1a and 111-1b and a reception electrodes 111-2a and 111-2b are used; but, transmission electrodes 111-1a and 111-1b may double with a function of reception electrodes by provision of a reflector of the SAW instead of a reception electrode electrodes 111-2a and 111-2b.

Also, in the above-described fifth to ninth embodiments, an electrode structure of the IDT 111 is not limited to the structure shown in the drawings and may be a unidirectional electrode (FEUDT: Floating electrode unidirectional transducers) or the like such as one having $\lambda/4$ or $\lambda/8$.

Tenth Embodiment

Hereinafter, an embodiment of the invention will be described in detail with reference to drawings.

In each embodiment described below, identical symbols are used for the elements which are identical to those described above, and the explanations thereof are omitted here.

Figure 13A:
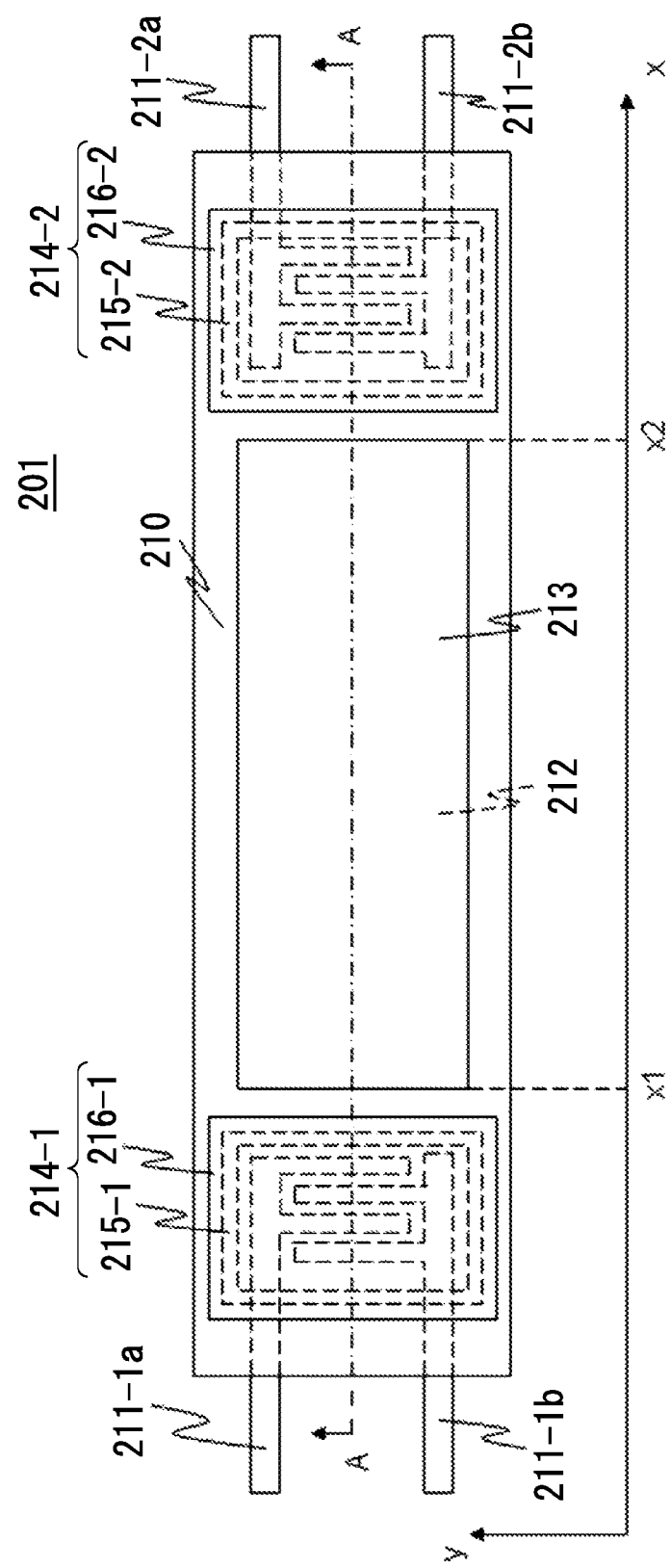
FIG. 13A is a schematic top view showing a SAW sensor according to a tenth embodiment.
Figure 13B:
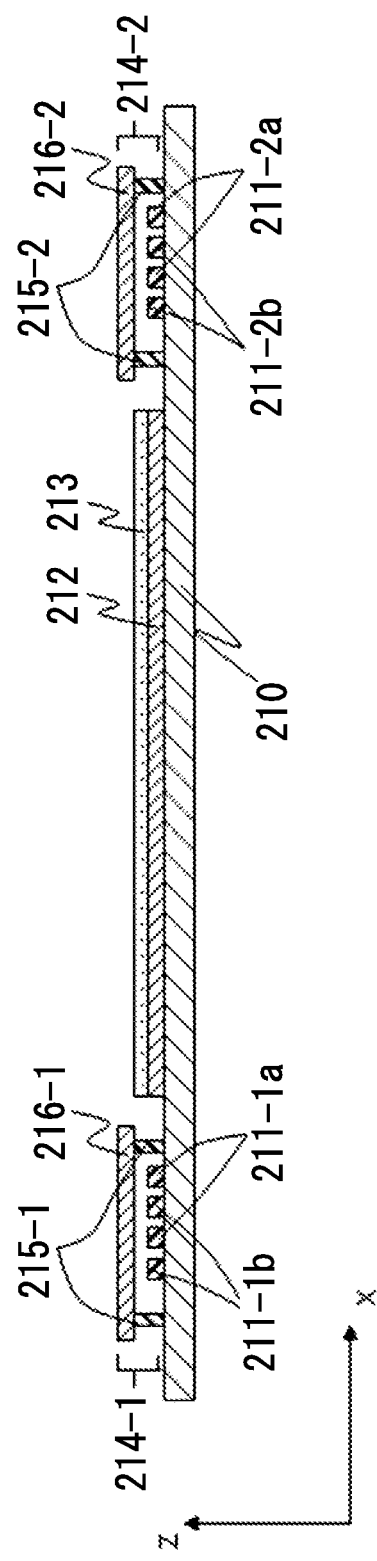
FIG. 13B is a schematic cross-sectional view showing the SAW sensor according to the tenth embodiment.

FIGS. 13A and 13B are schematic views showing a SAW sensor 201 used in the tenth embodiment of the invention.

FIG. 13A is a schematic top view showing the SAW sensor 201, and FIG. 13B is a schematic cross-sectional view showing the SAW sensor 201 as seen from the cutting plane A.

As shown in FIGS. 13A and 13B, the SAW sensor 201 is configured to include a piezoelectric element substrate 210 (piezo element), a transmission electrode 211-1a, a transmission electrode 211-1b, a reception electrode 211-2a, a reception electrode 211-2b, a reaction-region thin film 212, a porous base member 213, a sealing structure 214-1, and a sealing structure 214-2.

Moreover, in FIG. 13A, the longitudinal direction of the SAW sensor 201 (a propagation direction of the SAW) is represented by the x-axial direction and the lateral direction thereof is represented by the y-axial direction.

In FIG. 13B, the longitudinal direction of the SAW sensor 201 is represented by the x-axial direction and the thickness direction thereof is represented by the z-axial direction.

The piezoelectric element substrate 210 is a substrate that propagates a SAW (Surface Acoustic Wave; surface acoustic wave).

The piezoelectric element substrate 210 is, for example, a quartz substrate.

The transmission electrode 211-1a and the transmission electrode 211-1b are metal electrodes that constitute a transmission electrode and are formed of a comb-shaped pattern.

Hereinbelow, the transmission electrode 211-1a and the transmission electrode 211-1b are referred to as IDT 211-1.

In addition, the reception electrode 211-2a and the reception electrode 211-2b are metal electrodes that constitute reception electrode and is formed of a comb-shaped pattern.

Hereinbelow, the reception electrode 211-2a and the reception electrode 211-2b are collectively referred to as IDT 211-2.

The IDT 211-1 and the IDT 211-2 (collectively referred to as IDT 211) are electrodes that are formed on the piezoelectric element substrate 210.

The IDT 211 is a pair of facing electrodes.

The IDT 211 is configured of, for example, an aluminum thin film.

A burst signal serving as a transmitting signal is input to the IDT 211-1 from a burst circuit of a sense circuit which will be described later.

The IDT 211-1 excites a SAW corresponding to the input burst signal on the surface of the piezoelectric element substrate 210.

The IDT 211-2 receives the SAW that propagated along the surface of the piezoelectric element substrate 210 and converts it into a received electrical signal.

The IDT 211-2 outputs the converted electrical signal (referred to as a detection signal) to a phase-amplitude detecting circuit of the sense circuit.

The reaction-region thin film 212 is a thin film that is produced by vapor deposition of gold.

The reaction-region thin film 212 is a thin film having a surface on which an antibody is supported.

In particular, the antibody is supported by use of a well-known technique (for example, refer to Non-Patent Document "SH-SAW Biosensor for POCT", Yatsuda, Kogai, et al, Article 40 EM symposium, pp. 29 to 32, 2011.5.19).

The reaction-region thin film 212 is formed on the piezoelectric element substrate 210 and on the region between the paired IDTs 211 that are provided on the piezoelectric element substrate 210 so as to face each other.

The portion on which the piezoelectric element substrate 210 overlaps the reaction-region thin film 212 is a detection region into which liquid serving as an analyte is introduced (region serving as a sensor surface).

The porous base member 213 is a base member that is provided to be in contact with the reaction-region thin film 212.

The porous base member 213 is made of a substance such as cellulose nitrate.

The porous base member 213 is fixed so as to cover the reaction-region thin film 212.

For example, the porous base member 213 is fixed to be adhesively attached to the external four corners of the reaction-region thin film 212.

The porous base member 213 holds solution that drops thereon and allows the solution to infiltrate into the inside thereof and the surface thereof.

The porous base member 213 transfers the solution, that dropped thereon, to the inside of the porous base member 213 and the surface of the reaction-region thin film 212 due to a capillary phenomenon, and holds it.

That is, the SAW sensor 201 holds the solution drop inside the porous base member 213 and on the surface of the reaction-region thin film 212.

Moreover, as shown in FIG. 13A, the porous base member 213 is disposed between the positions x1 and x2 in the x-axial direction.

In the SAW sensor 201, the solution that is transported to the inside of the porous base member 213 makes a specified area of the reaction-region thin film 212 wet.

Here, the specified area is a region having a surface area defined by the portion on which the porous base member 213 overlaps the reaction-region thin film 212.

For example, in the case of covering the entire surface of the reaction-region thin film 212 with the porous base member 213, it means the entire region of the reaction-region thin film 212.

An antigen in solution reacts with an antibody that is supported on the reaction-region thin film 212, and an antigen antibody complex is thereby generated on a specified region of the reaction-region thin film 212.

That is, in the reaction-region thin film 212, as a result of dropping a liquid sample including an antigen on the top surface thereof, an antigen-antibody reaction occurs between the antibody that is supported on the reaction-region thin film 212 and the antigen of the liquid sample.

Consequently, an antigen antibody complex in which the antibody that is supported on the reaction-region thin film 212 and the antigen are combined is produced on the reaction-region thin film 212.

In other cases, even other than gold, various materials may be adopted as a material used to form the reaction-region thin film 212 as long as the material can support an antibody.

Additionally, as shown in FIGS. 13A and 13B, the porous base member 213 may overlap the reaction-region thin film 212 so as to have the same surface area when seen in a plan view or may be disposed to have a small surface area so as to be located inside of the reaction-region thin film 212 when seen in a plan view.

The porous base member 213 is only necessary to be disposed so as to cover the specified region of the reaction-region thin film 212.

The sealing structure 214-1 of the transmission electrode (disposed at the position close to the transmission electrode) includes a sealing wall 215-1 and a seal ceiling 216-1.

The sealing wall 215-1 is a wall that covers the IDT 211-1 and is formed on the piezoelectric element substrate 210 in a rectangle shape.

The sealing wall 215-1 is formed from, for example, photosensitive resin.

Furthermore, the seal ceiling 216-1 is a ceiling that occludes the upper side of the sealing wall 215-1 and thereby tightly seals the IDT 211-1 from the exterior.

The seal ceiling 216-1 is disposed at the upper side of the sealing wall 215-1 so that the sealing wall 215-1 is located in the flat surface region of the seal ceiling 216-1.

The seal ceiling 216-1 is formed of, for example, a glass substrate.

In particular, an adhesive layer which is not shown in the figure is provided between the sealing wall 215-1 and the seal ceiling 216-1, and adhesively attaches the sealing wall 215-1 to the seal ceiling 216-1 by tight sealing.

The sealing structure 214-1 is a sealing structure that covers and tightly seals the IDT 211-1 from the exterior so as to form a space above the IDT 211-1 and prevents the IDT 211-1 from coming into contact with liquid.

Additionally, similar to the sealing structure 214-1, the sealing structure 214-2 of the reception electrode (provided at the position close to the reception electrode) is a sealing structure that includes a sealing wall 215-2 and a seal ceiling 216-2, covers and tightly seals the IDT 211-2 from the exterior so as to form a space above the IDT 211-2, and prevents the IDT 211-2 from coming into contact with liquid.

Even where there is a variation in an atmosphere (for example, degree of humidity) in the detection region, as a result of adopting the sealing structure 214-1 and the sealing structure 214-2, the IDT 211-1 and the IDT 211-2 are less easily affected by the variation thereof.

Furthermore, in FIGS. 13A and 13B, the porous base member 213 is disposed so as to overlap the sealing structure 214-1 and the seal ceiling of the sealing structure 214-2; however, it is not necessary to arrange the porous base member 213 so as to overlap the seal ceiling as long as it is disposed so as to cover the detection region of a sensor on which the reaction-region thin film 212 is placed.

Particularly, in the case of arranging the porous base member 213 so as not to overlap the seal ceiling, even where the porous base member 213 is significantly displaced in a direction in which a surface acoustic wave propagates (displacement), since the sealing structure 214-1 and the sealing structure 214-2 protect the IDT 211-1 and the IDT 211-2, respectively, the IDT is not wet with solution, it does not affect an operation of transmitting an elastic wave or an operation of receiving an elastic wave of the IDT.

FIG. 3 is a schematic block diagram illustrating a sense circuit 20 used in solution measurement using the SAW sensor 201.

As shown in FIG. 2, the sense circuit 20 is configured to include the SAW sensor 201, an alternating-current signal source 21, the burst circuit 22, the phase-amplitude detecting circuit 23, and a PC 24 (Personal Computer).

The alternating-current signal source 21 generates a sine wave alternating-current signal of, for example, 250 MHz.

The alternating-current signal source 21 outputs the generated alternating-current signal to the burst circuit 22.

The burst circuit 22 converts the alternating-current signal that is input from the alternating-current signal source 21 into a periodic burst signal.

Here, the period of the burst signal is set to be longer than a time required for propagation of the SAW from the IDT 211-1 to the IDT 211-2 of the surface of the piezoelectric element substrate 210.

The burst circuit 22 outputs the generated burst signal to the IDT 211-1 and the phase-amplitude detecting circuit 23 of the SAW sensor 201.

In other cases, in the case where a disturbing signal such as noise including a direct wave, other bulk wave, or the like with the exception of a main signal included in the signal output from the SAW sensor 201 is sufficiently low, the burst circuit 22 is not necessary, and a continuous wave may be used.

Based on a detection signal input from the IDT 211-2 of the SAW sensor 201 and the burst signal input from the burst circuit 22, the phase-amplitude detecting circuit 23 calculates a phase variation and an amplitude change which are associated with a propagation time that is a time required for propagation of the SAW on the piezoelectric element substrate 210.

Specifically, the phase-amplitude detecting circuit 23 detects a phase variation and attenuation of amplitude which is associated with a required propagation time between the inputting of the burst signal and the inputting of the detection signal.

The phase-amplitude detecting circuit 23 outputs the detected phase variation and the attenuation of amplitude to the PC 24.

Based on the phase variation and the attenuation of amplitude which are input from the phase-amplitude detecting circuit 23, the PC 24 determines an amount of and the kind of an antibody on the surface and a specifically-reacted antigen in solution and displays the determination result.

Next, a state where a solution is infiltrating on the porous base member 213 when an antibody that is contained in the solution is measured will be described.

Figure 14A:
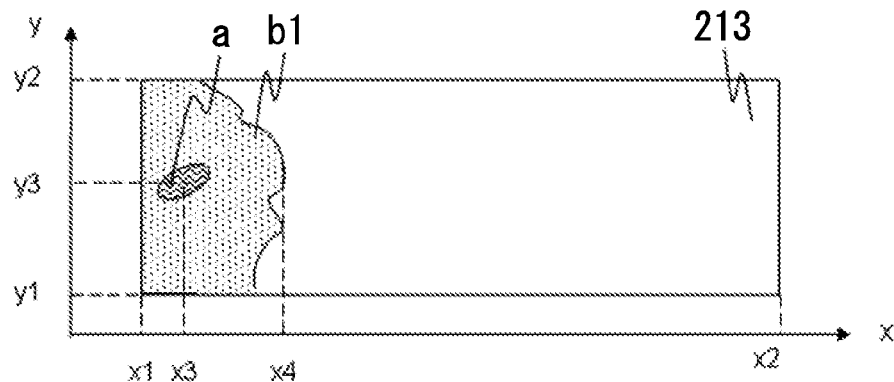
FIG. 14A is a view illustrating a state where a solution is infiltrating on a porous base member according to the tenth embodiment.
Figure 14B:
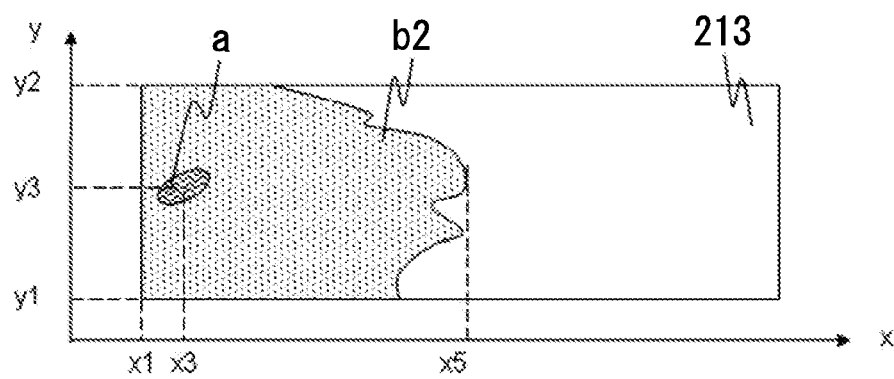
FIG. 14B is a view illustrating a state where a solution is infiltrating on a porous base member according to the tenth embodiment.
Figure 14C:
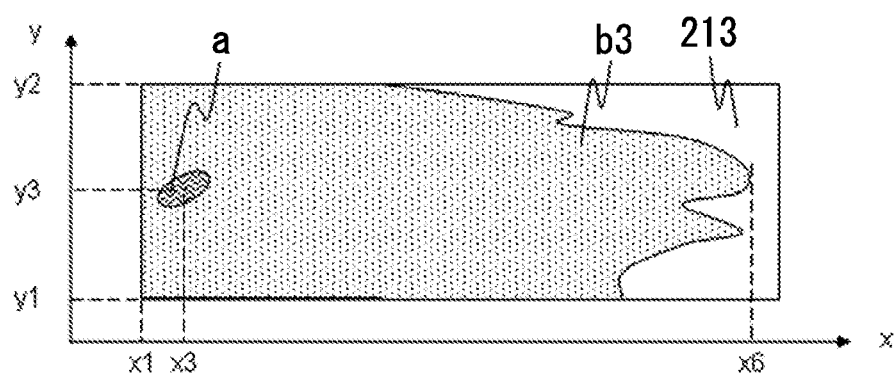
FIG. 14C is a view illustrating a state where a solution is infiltrating on a porous base member according to the tenth embodiment.

FIGS. 14A to 14C are views illustrating an infiltration state of the solution on the porous base member 213 according to the tenth embodiment.

FIG. 14A is a view illustrating an infiltration state of the solution on the porous base member 213 at a time point t1.

FIG. 14B is a view illustrating an infiltration state of the solution on the porous base member 213 at a time point t2 (t2 is greater than t1).

FIG. 14C is a view illustrating an infiltration state of the solution on the porous base member 213 at a time point t3 (t3 is greater than t2).

In FIGS. 14A to 14C, a longitudinal direction of the porous base member 213 is represented as the x-axial direction and the lateral direction thereof is represented as the y-axial direction.

In FIGS. 14A to 14C, positions x1 and x2 of the porous base member 213 are the same as the positions shown in FIG. 13A.

As shown in FIGS. 14A to 14C, a measurer of the SAW sensor 201 drops solution a on the position (x3, y3) by use of, for example, a micropipette which is not shown in the figure.

The porous base member 213 transfers the solution a, that dropped thereon, to the inside of the porous base member 213 and the surface of the reaction-region thin film 212 due to a capillary phenomenon in the x-axial positive direction, and holds it.

The solution a that dropped on the porous base member 213 gradually infiltrates into the inside of the porous base member 213 and the surface of the porous base member 213 in the x-axial positive direction.

Because of this, at a time point t1, the end of the region b1 (hereinbelow, refer to an infiltrating region) into which the introduced solution a infiltrates to reach the position x4 in the x-axial direction as shown in FIG. 14A.

Furthermore, at a time point t2, the end of the infiltrating region b2 infiltrates to reach the position x5 (x5 is greater than x4) in the x-axial direction as shown in FIG. 14B.

Furthermore, at a time point t3, the end of the infiltrating region b3 infiltrates to reach the position x6 (x6 is greater than x5) in the x-axial direction as shown in FIG. 14C.

In addition, an antigen in solution gradually reacts with the antibody, that is supported on the reaction-region thin film 212, in accordance with the infiltration of the solution and thereby generates an antigen antibody complex on the reaction-region thin film 212.

Subsequently, temporarily, a case will be described where solution directly drops on the reaction-region thin film 212 of the SAW sensor 201.

As shown in FIGS. 13A and 13B, in the case where, temporarily, solution directly drops on the reaction-region thin film 212 of the SAW sensor 201, the solution infiltrates into the entirety of the reaction-region thin film 212.

The SAW is an acoustic wave that concentrates in the vicinity of the surface of the piezoelectric element substrate 210 (the position close to the surface) and propagates.

When a substance adsorbs onto the top surface of the piezoelectric element substrate 210, a mass per unit volume and a degree of viscosity of the top surface thereof vary.

According to variations in a mass and a degree of viscosity, a propagation velocity of the SAW varies, and attenuation of amplitude of the SAW varies.

The phase-amplitude detecting circuit 23 of the sense circuit 20 measures an antigen that is contained in solution utilizing the variation in phase and the variation in attenuation of amplitude.

In the case where a concentration of the antigen contained in solution is low, since an antigen-antibody reaction occurs at a portion of the reaction-region thin film 212, a detection signal is not saturated.

Because of this, the phase-amplitude detecting circuit 23 of the sense circuit 20 can detect a phase variation and an amplitude change which are associated with a propagation time that is a time required for propagation of the SAW on the piezoelectric element substrate 210.

On the other hand, in the case where a concentration of the antigen contained in solution is high, since an antigen-antibody reaction occurs at over the entirety of the reaction-region thin film 212, a detection signal is saturated.

Because of this, the phase-amplitude detecting circuit 23 of the sense circuit 20 cannot detect a phase variation and an amplitude change which are associated with a propagation time.

For this reason, in the tenth embodiment, solution does not directly drop on the reaction-region thin film 212, and solution drops on a porous base member 213 in which the solution infiltrates thereinto for a long time longer than the case of directly dropping the solution on the reaction-region thin film 212.

The solution that dropped on the porous base member 213 infiltrates thereinto in the x-axial positive direction at every time point as shown in FIGS. 14A and 14B.

Consequently, even where a concentration of an antigen in solution is high, since the solution does not infiltrate into the above of the reaction-region thin film 212 at one time, the phase-amplitude detecting circuit 23 can detect a phase variation and an amplitude change, which are associated with a propagation time, at every time point.

Next, measurement using the sense circuit 20 will be described.

At first, a measurer drops a solvent, that does not contain an antigen, on the position (x3, y3) shown in FIGS. 14A to 14C and thereby causes the solvent to infiltrate onto the top of the reaction-region thin film 212, and measures a phase variation which is associated with a propagation time of the SAW (blank test).

Next, the measurer replaces the SAW sensor 201 with another sample (SAW sensor 201), drops the solution of the sample containing an antigen on the position (x3, y3) shown in FIG. 14A, and measures a phase variation which is associated with the propagation time thereof.

A difference between the phase variation corresponding to the solvent and the phase variation corresponding to the solution is a variation in phase which is caused by an antigen antibody complex that is generated in the reaction-region thin film 212 due to an antigen-antibody reaction.

The PC 24 has stored the phase variation of the blank test in memory, calculates a difference between the phase variation and a phase variation obtained by dropping of solution, and thereby calculates a variation in phase.

The PC 24 identifies an antigen contained in solution based on the variation in phase.

Similarly, attenuation of amplitude identifies an antigen contained in solution based on the variation in attenuation of amplitude.

Furthermore, even in the case where the propagation time of the SAW in the solvent to be used is not determined in advance, the phase and the amplitude which are immediately after dropping of solution containing an antigen are used as a reference, the amount of and the kind of antigen in solution is determined as a result of obtaining a difference between subsequent changes based thereon, and the determination result may be displayed.

As described above, in the tenth embodiment, the SAW sensor 201 is configured to the porous base member 213, that requires an infiltration time longer the length of time of converting a surface acoustic wave into an electrical signal or converting an electrical signal into a surface acoustic wave, on the reaction-region thin film 212.

Because of this, the SAW sensor 201 can output a detection signal for a long period of time.

Moreover, in the SAW sensor 201, an intensity of a detection signal becomes lower than the case where solution comes into contact with the reaction-region thin film 212 at the same time.

As a result, even in the case of measuring solution having a high concentration, since the SAW sensor 201 can output the detection signal without being saturated, accurate measurement can be carried out.

Particularly, the case is described where the reaction-region thin film 212 supports an antibody in the tenth embodiment, the reaction-region thin film 212 may not support an antibody.

Even in this case, it is possible to carry out comparison of the characteristics of solutions, such as whether a concentration of solution is high or low, or whether or not a solution includes an antigen.

Eleventh Embodiment

Hereinafter, an eleventh embodiment of the invention will be described in detail with reference to drawings.

In the eleventh embodiment, the case will be described where antibodies different from each other are dispersed in a porous base member.

Particularly, the sense circuit 20 is configured so that the SAW sensor 201 in FIG. 3 shown in the first embodiment is replaced with the SAW sensor 201a of the eleventh embodiment.

Figure 15A:
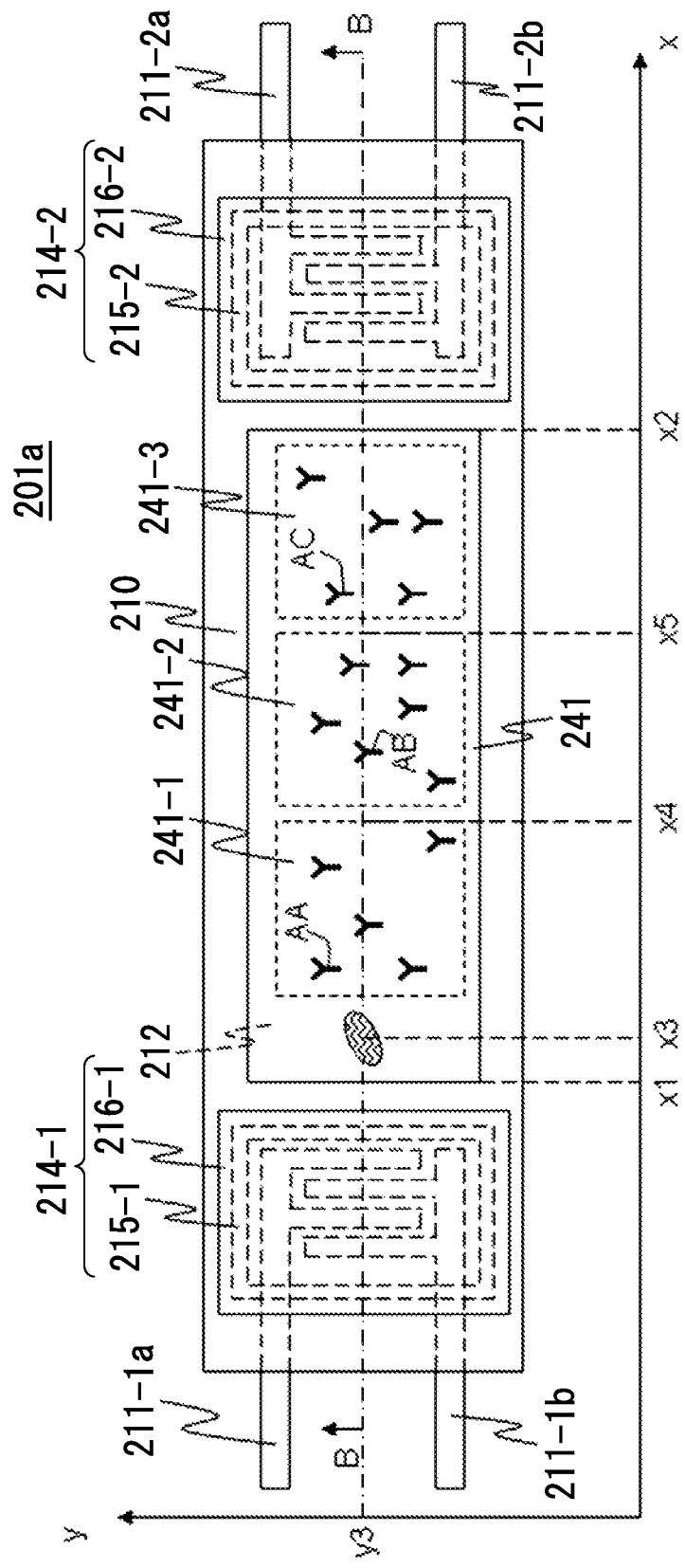
FIG. 15A is a schematic top view showing the configuration of a SAW sensor according to an eleventh embodiment.
Figure 15B:
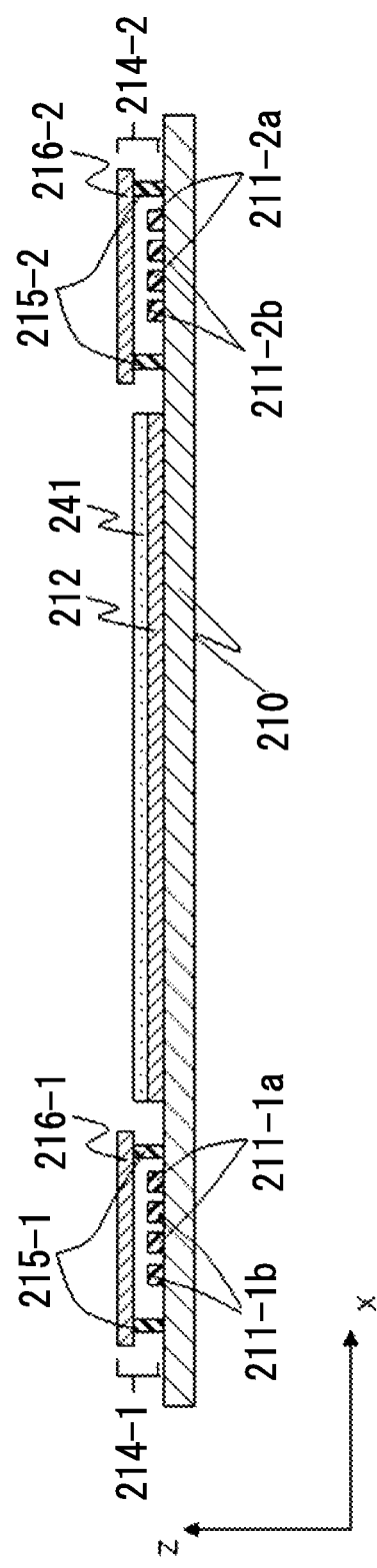
FIG. 15B is a schematic cross-sectional view showing the configuration of the SAW sensor according to the eleventh embodiment.

FIGS. 15A and 15B are schematic views showing a configuration of the SAW sensor 201a according to the eleventh embodiment.

FIG. 15A is a schematic top view showing the SAW sensor 201a, and FIG. 15B is a schematic cross-sectional view showing the SAW sensor 201a as seen from the cutting plane B.

In FIG. 15A, the longitudinal direction of the SAW sensor 201a is represented by the x-axial direction and the lateral direction thereof is represented by the y-axial direction.

In FIG. 15B, the longitudinal direction of the SAW sensor 201a is represented by the x-axial direction and the thickness direction thereof is represented by the z-axial direction.

As shown in FIGS. 15A and 15B, the SAW sensor 201a is configured to include the piezoelectric element substrate 210, the transmission electrode 211-1a, the transmission electrode 211-1b, the reception electrode 211-2a, the reception electrode 211-2b, the reaction-region thin film 212, the porous base member 241, the sealing structure 214-1, and the sealing structure 214-2.

The porous base member 241 is configured to include a porous base member 241-1 having a first antibody AA that is dispersed therein and represented by reference letter AA, a porous base member 241-2 having a first antibody AB that is dispersed therein and represented by reference letter AB, and a porous base member 241-3 having a first antibody AC that is dispersed therein and represented by reference letter AC.

Furthermore, the antibody AA, the antibody AB, and the antibody AC are first antibodies different from each other.

When solution drops on the position (x3, y3) on the top surface of the porous base member 241, the solution that dropped thereon infiltrates into the inside of the porous base member 241 and infiltrates into the porous base member 241 in the x-axial positive direction.

Here, as an example, the case will be described where solution drops on the position (x3, y3) on the porous base member 241 at a time point to.

At a time point t1, the solution infiltrates to reach the position x4 in the x-axial direction.

Since the solution infiltrates into the region of the porous base member 241-1, it reacts with the first antibody AA in the porous base member 241-1.

The antigen-antibody complex generated by the reaction reacts with the second antibody that is supported on the reaction-region thin film 212.

Next, at a time point t2, the solution infiltrates to reach the position x5 in the x-axial direction.

Since the solution infiltrates into the region of the porous base member 241-2, it reacts with the first antibody AB in the porous base member 241-2.

The antigen-antibody complex generated by the reaction reacts with the second antibody that is supported on the reaction-region thin film 212.

Next, at a time point t3, the solution infiltrates to reach the position x2 in the x-axial direction.

Since the solution infiltrates into the region of the porous base member 241-3, it reacts with the first antibody AC in the porous base member 241-3.

The antigen-antibody complex generated by the reaction reacts with the second antibody that is supported on the reaction-region thin film 212.

The phase-amplitude detecting circuit 23 sequentially observes a detection signal that is detected by the reaction generated in the porous base member 241-1, a detection signal that is detected by the reaction generated in the porous base member 241-2, and a detection signal that is detected by the reaction generated in the porous base member 241-3, with a delay corresponding to the infiltration velocity of the solution.

Accordingly, the eleventh embodiment includes the piezoelectric element substrate 210 that propagates a surface acoustic wave, the IDT 211 that carries out conversion of an electrical signal and a surface acoustic wave, and the porous base member 241 which comes into contact with the piezoelectric element substrate 210 and into which liquid having reactants, that react with the respective different targets and are dispersed therein, infiltrates in liquid infiltration directions.

Consequently, it is possible to detect reactions which are due to different antibodies at different time points, and it is possible to detect a plurality of samples by use of one SAW sensor 201a and one porous base member 241.

In other cases, the porous base members 241-1, 241-2, and 241-3 may be part of a common porous base member 241 or may be a base member that is newly provided on a common porous base member 241.

In the case where a plurality of kinds of antigens are contained in the solution that is dropped on the porous base members 241-1, 241-2, and 241-3, antigen-antibody combined bodies are generated at the respective portions in which antibodies corresponding to the respective antigens are dispersed.

Particularly, in the eleventh embodiment, the porous base member 241, in which three kinds of antibodies different from each other are dispersed, is illustrated as an example; however, as the number of kinds of antibodies, any number may be used as long as it is more than one.

Twelfth Embodiment

Hereinafter, a twelfth embodiment of the invention will be described in detail with reference to drawings.

In the twelfth embodiment, the case will be described where a porous base member has regions having different infiltration rates of solutions.

Figure 16A:
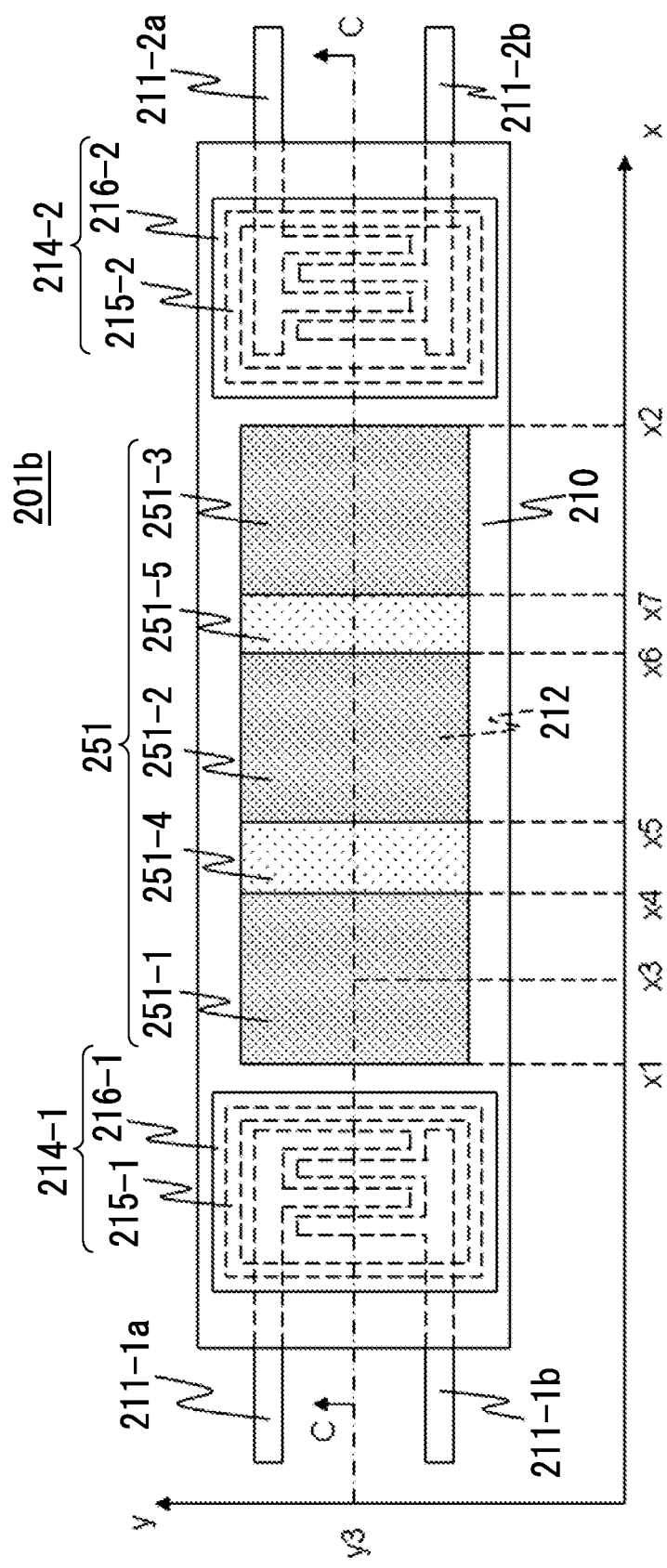
FIG. 16A is a schematic top view showing a configuration of a SAW sensor according to a twelfth embodiment.
Figure 16B:
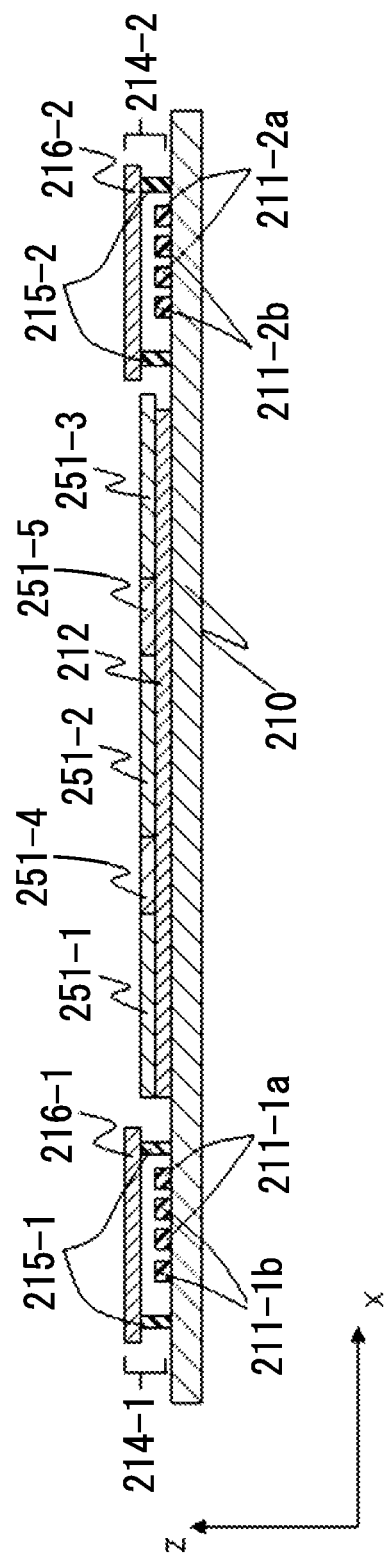
FIG. 16B is a schematic cross-sectional view showing the configuration of the SAW sensor according to the twelfth embodiment.

FIGS. 16A and 16B are schematic views showing a configuration of a SAW sensor 201b according to the twelfth embodiment.

FIG. 16A is a schematic top view showing the SAW sensor 201b, and FIG. 16B is a schematic cross-sectional view showing the SAW sensor 201b as seen from the cutting plane C.

In FIG. 16A, a longitudinal direction of the SAW sensor 201b is represented as the x-axial direction and the lateral direction thereof is represented as the y-axial direction.

In FIG. 16B, the longitudinal direction of the SAW sensor 201b is represented by the x-axial direction and the thickness direction thereof is represented by the z-axial direction.

As shown in FIGS. 16A and 16B, the SAW sensor 201b is configured to include the piezoelectric element substrate 210, the IDT 211, the reaction-region thin film 212, and a porous base member 251.

The porous base member 251 is configured to include a porous base members 251-1, 251-2, and 251-3 (first region) having a first infiltration rate and a porous base members 251-4 and 251-5 (second region) having a second infiltration rate.

For example, the infiltration rate, at which the solutions infiltrate into the porous base members 251-4 and 251-5 in a predetermined distance, is 1/10 of the infiltration rate of the porous base members 251-1, 251-2, and 251-3.

As shown in FIG. 16A, a length of the porous base member 251-1 in the x-axial direction is x4-x1, a length of the porous base member 251-2 in the x-axial direction is x6-x5, and a length of the porous base member 251-3 in the x-axial direction is x2-x7.

Additionally, a length of the porous base member 251-4 in the x-axial direction is x5-x4, and a length of the porous base member 251-5 in the x-axial direction is x7-x6.

The lengths of the porous base members 251-4 and 251-5 in the x-axial direction may be shorter than the lengths of the porous base members 251-1, 251-2, and 251-3 in the x-axial direction.

Next, the case will be described where a solution drops into the position (x3, y3) in the x-axial direction on the porous base member 251-1 at a time point t1.

Infiltration of a solution promptly occurs in the porous base member 251-1, and the reaction-region thin film 212 corresponding to the surface area of the porous base member 251-1 becomes infiltrated.

At a time point t1, the solution infiltrates into the porous base member 251-4 over the position x4 of the porous base member 251-1 in the x-axial direction, the infiltration rate is extremely slow as compared with that in the porous base member 251-1.

Accordingly, in the period from the time point t1 to the time point t2, that is, until the solution reaches the porous base member 251-2, the SAW sensor 201b exclusively detects the reaction of the antibody supported by the reaction-region thin film 212 that comes into contact with the antigen-antibody combined body generated in the porous base member 251-1 or the porous base member 251-1.

At a time point t2, when a solution reaches the position x5 of the porous base member 251-2 in the x-axial direction, it promptly infiltrates into the porous base member 251-2.

For this reason, the SAW sensor 201b simultaneously detects the reactions that occurs at the porous base member 251-1 and the porous base member 251-2.

The sense circuit 20 calculates a difference between the detection signal of the porous base member 251-1 and the detection signal of the porous base member 251-2 and thereby detects a signal which is due to the reaction that occurs at the porous base member 251-2.

As described below, at a time point t2, the solution infiltrates into the porous base member 251-5 over the position x6 the porous base member 251-2 in the x-axial direction.

Furthermore, at a time point t3, when solution reaches the position x7 of the porous base member 251-3 in the x-axial direction, it promptly infiltrates into the porous base member 251-3.

At a time point t3, the SAW sensor 201b simultaneously detects the reactions that occurs at the porous base member 251-1, the porous base member 251-2, and the porous base member 251-2.

The sense circuit 20 calculates a difference between the detection signal of the detection signal of the porous base member 251-1, the porous base member 251-2, and the porous base member 251-3 and thereby detects a signal which is due to the reaction that occurs at the porous base member 251-3.

In the sense circuit 20, it is necessary to detect a degree of traveling of the dropped solution in the x-axial direction.

The above degree of traveling is detected by use of, for example, two SAW sensors 201b shown in FIGS. 16A and 16B.

In this case, the porous base members 251-1, 251-2, and 251-3 of one of SAW sensor 201b-1 support first antibodies.

The porous base members 251-1, 251-2, and 251-3 of the other SAW sensor 201b-2 do not support first antibodies.

With this configuration, the SAW sensor 201b-1 detects an antigen in the dropped solution, and the SAW sensor 201b-2 does not detect an antigen in the dropped solution.

Consequently, it is possible to detect the degree of viscosity of the solution in the SAW sensor 201b-2.

The measurer simultaneously drops the same amount of a solution on the respective positions (x3, y3) of two the SAW sensors 201b-1 and 201b-2.

The sense circuit 20 may be configured to detect a degree of traveling of solution by measuring the two SAW sensors 201b-1 and 201b-2.

As described above, in the twelfth embodiment, the porous base member 251 has a structure in which the porous base members 251-1, 251-2, and 251-3 having a fast infiltration rate and the porous base members 251-4 and 251-5 having a slow infiltration rate are alternately repeated.

By means of this structure, it is possible to detect analyte by time division, which is contained in solution.

Additionally, in the above-described tenth to twelfth embodiments, the transmission electrodes 211-1a and 211-1b and the reception electrodes 211-2a and 211-2b are used; but, the transmission electrodes 211-1a and 211-1b may double with a function of a reception electrode by provision of a reflector of the SAW instead of the reception electrodes 211-2a and 211-2b.

As a reflector, for example, a grating reflection unit may be used.

In the twelfth embodiment, in the case where a reflector of the SAW is provided instead of the reception electrodes 211-2a and 211-2b and the transmission electrodes 211-1a and 211-1b double with a function of a reception electrode, the porous base members 251-4 and 251-5 having a slow infiltration rate also function as a reflector.

Consequently, a surface acoustic wave that returns to the transmission electrodes 211-1a and 211-1b includes a reflected wave which is caused by the reflector of the SAW instead of the reception electrodes 211-2a and 211-2b, a reflected wave which is caused by the porous base member 251-4, and a reflected wave which is caused by the porous base member 251-5.

For this reason, since it is necessary to identify the reflected waves, lengths of the porous base members 251-1, 251-2, and 251-3 in the x-axial direction may be varied so that the reflected waves of the respective regions do not overlap.

Alternatively, lengths of the porous base members 251-4 and 251-5 in the x-axial direction may vary.

Moreover, in the aforementioned tenth to twelfth embodiments, the piezoelectric element substrate 210 may be a material made of a substance exhibiting a piezoelectric effect such as lithium tantalate, lithium niobate, or lithium tetraborate.

Additionally, in the above-described tenth to twelfth embodiments, even other than aluminum, other materials may be adopted as a material used to form the IDT 211 as long as the material is a high conductive metal.

Furthermore, the above-mentioned tenth to twelfth embodiments shows as an example that, the reaction-region thin film 212 supports an antibody and measures an antigen; and if it is not used to measure an antigen, it is not necessary to provide the reaction-region thin film 212.

Hereinbefore, the embodiments of the invention are described with reference to drawings, however, specific configurations are not limited to the above-mentioned embodiments, and various design modifications or the like may be made without departing from the scope of the invention.

DESCRIPTION OF REFERENCE NUMERAL

1, 1B, 1C, 1D, 101, 101A, 101B, 101C, 101D, 201 SAW sensor
10, 110, 210 piezoelectric element substrate (piezo element)
11, 61A, 61B, 71A, 71B, 71C electrode
12, 112, 212 reaction-region thin film
13, 13B, 73, 113, 113B, 173, 213, 241, 241-1, 241-2, 241-3, 251, 251-1, 251-2, 251-3, 251-4, 251-5 porous base member
13B-1, 113B-1 filter layer
13B-2, 113B-2 reaction layer
13B-3, 113B-3 water retention layer
114A-1, 114A-2 hydrophobic base member
14 sealing structure
17 micropipette
20 sense circuit
21 alternating-current signal source
22 burst circuit
23 phase-amplitude detecting circuit
62-1 short-circuiting reaction region
62-2 open reaction region
111, 111-1a, 111-1b, 111-2a, 111-2b, 161A, 161B, 161A-1a, 161A-1b, 161A-2a, 161A-2b, 161B-1a, 161B-1b, 161B-2a, 161B-2b, 171A, 171A-1a, 171A-1b, 171A-2a, 171A-2b, 171B, 171B-1a, 171B-1b, 171B-2a, 171B-2b, 171C, 171C-1a, 171C-1b, 171C-2a, 171C-2b, 211, 211-1a, 211-1b, 211-2a, 211-2b IDT
20 sense circuit
21 alternating-current signal source
22 burst circuit
23 phase-amplitude detecting circuit
24 PC
162-1 short-circuiting reaction region
162-2 open reaction region

The invention claimed is:

1. A surface acoustic wave sensor comprising:
a piezo element that propagates a surface acoustic wave;
an electrode that carries out conversion of an electrical signal and a surface acoustic wave;
a porous base member which is disposed at a propagation path of the surface acoustic wave and which allows liquid to infiltrate into an inside thereof and a surface thereof and holds the liquid thereinside; and
a reaction-region thin film including: a surface that holds the liquid; a specified area having a surface area defined by a portion on which the porous base member overlaps the reaction-region thin film; and a detection region on which the piezo element overlaps the reaction-re ion thin film the specified area coming into contact with the liquid, the detection region coming into contact with the liquid.

2. The surface acoustic wave sensor according to claim 1, further comprising a sealing structure that prevents the electrode from coming into contact with liquid.

3. The surface acoustic wave sensor according to claim 2, wherein
the porous base member has a portion that does not overlap the detection region in a plan view.

4. The surface acoustic wave sensor according to claim 1, wherein
the porous base member includes at least one of a reaction layer including a substance that reacts with a target and a filter layer that removes other than a target.

5. The surface acoustic wave sensor according to claim 2, wherein
the electrode is constituted of two electrode pairs, and
the detection region has a short-circuiting reaction region that is electrically connected to one of the two electrode pairs and an open reaction region that is not electrically connected to the other of the two electrode pairs.

6. The surface acoustic wave sensor according to claim 2, wherein
the electrode is constituted of a plurality of electrode pairs, and a separate reactant that reacts with a target in each electrode pair is provided on the porous base member that is provided between the electrode pairs.

7. The surface acoustic wave sensor according to claim 1, wherein
the electrode is constituted of two electrode pairs, and
the porous base member comes into contact with the piezo element with a thin film interposed therebetween and is connected to the porous base member, and a portion thereof which comes into contact with each electrode is made of a hydrophobic base member.

8. The surface acoustic wave sensor according to claim 7, wherein
the porous base member has a portion that does not come into contact with the piezo element.

9. The surface acoustic wave sensor according to claim 7, wherein
the porous base member includes at least one of a reaction layer including a substance that reacts with a target and a filter layer that removes other than a target.

10. The surface acoustic wave sensor according to claim 7, wherein
the piezo element includes:
a first portion having a region that is not electrically connected to the electrode; and a second portion having a thin film that is electrically connected to the electrode.

11. The surface acoustic wave sensor according to claim 7, wherein
the electrode is constituted of a plurality of electrode pairs, and a reactant that reacts with a target in each electrode pair is provided on the porous base member that is provided between the electrode pairs.

12. The surface acoustic wave sensor according to claim 7, further comprising:
a detection region which is disposed at a propagation path of the surface acoustic wave, into which liquid serving as an analyte is introduced, wherein
the porous base member comes into contact with the detection region, and
liquid infiltrates into the porous base member due to a capillary phenomenon.

13. The surface acoustic wave sensor according to claim 12, wherein
the porous base member allows liquid to infiltrate thereinto due to a capillary phenomenon in a propagation direction of the surface acoustic wave.

14. The surface acoustic wave sensor according to claim 12, wherein
separate reactants which react with a target are formed and dispersed in directions in which the solution infiltrates into the porous base member.

15. The surface acoustic wave sensor according to claim 12, wherein
the porous base member includes a first region and a second region,
the first region and the second region are alternately formed in a propagation direction of the surface acoustic wave, and
an infiltration rate in the first region is greater than an infiltration rate in the second region.

16. The surface acoustic wave sensor according to claim 15, wherein
in the porous base member, lengths in the propagation direction of the surface acoustic wave in a plurality of the first regions are different from each other.

17. The surface acoustic wave sensor according to claim 15, wherein
in the porous base member, lengths in the propagation direction of the surface acoustic wave in a plurality of the second regions are different from each other.

18. The surface acoustic wave sensor according to claim 1, wherein
two electrodes are provided, and the detection region has a short-circuiting reaction region that is electrically connected to one of the two electrodes and an open reaction region that is not electrically connected to the other of the two electrodes.

19. The surface acoustic wave sensor according to claim 1, wherein
the porous base member allows liquid to infiltrate thereinto due to a capillary phenomenon in a propagation direction of the surface acoustic wave.

20. The surface acoustic wave sensor according to claim 1, wherein
separate reactants which react with a target are formed and dispersed in directions in which the solution infiltrates into the porous base member.

21. The surface acoustic wave sensor according to claim 1, wherein
the porous base member includes at least one of a reaction layer including a substance that reacts with a target and a filter layer that removes other than a target.

22. The surface acoustic wave sensor according to claim 1, wherein
the porous base member has a portion that does not come into contact with the piezo element.

23. The surface acoustic wave sensor according to claim 1, wherein
a plurality of electrodes are provided, and a reactant that reacts with a target is provided on the porous base member that is provided so as to correspond to each of the electrodes.

24. The surface acoustic wave sensor according to claim 1, wherein
a plurality of electrodes are provided, and reactants that react with each other are provided on each porous base member.

25. The surface acoustic wave sensor according to claim 1, wherein
two electrodes are provided, and the porous base member comes into contact with the piezo element with a thin film interposed therebetween, is connected to the porous base member, and has a portion that comes into contact with each electrode is formed of a hydrophobic base member.

26. The surface acoustic wave sensor according to claim 10, wherein
the piezo element includes:
a first portion having a region that is not electrically connected to the electrode; and
a second portion having a thin film that is electrically connected to the electrode.

27. The surface acoustic wave sensor according to claim 1, wherein
the porous base member includes a first region and a second region,
the first region and the second region are alternately formed in a propagation direction of the surface acoustic wave, and
an infiltration rate in the first region is greater than an infiltration rate in the second region.

28. The surface acoustic wave sensor according to claim 13, wherein
in the porous base member, lengths in the propagation direction of the surface acoustic wave in a plurality of the first regions are different from each other.

29. The surface acoustic wave sensor according to claim 13, wherein
in the porous base member, lengths in the propagation direction of the surface acoustic wave in a plurality of the second regions are different from each other.

* * * * *

UNITED STATES PATENT AND TRADEMARK OFFICE
CERTIFICATE OF CORRECTION

PATENT NO. : 9,678,042 B2
APPLICATION NO. : 14/355581
DATED : June 13, 2017
INVENTOR(S) : Takashi Kogai et al.

Page 1 of 1

It is certified that error appears in the above-identified patent and that said Letters Patent is hereby corrected as shown below:

In the Claims

Column 36, Line 28, Claim 4:
4. The surface acoustic wave sensor according to claim 1, ...other than a target.
Should read:
4. The surface acoustic wave sensor according to claim 2, ... other than a target.

Signed and Sealed this
Twelfth Day of January, 2021

Andrei Iancu
*Director of the United States Patent and Trademark Office*